(12) United States Patent
Li et al.

(10) Patent No.: US 9,933,341 B2
(45) Date of Patent: Apr. 3, 2018

(54) SAMPLE PREPARATION FOR FLOW CYTOMETRY

(71) Applicant: Becton, Dickinson and Company, Franklin Lakes, NJ (US)

(72) Inventors: Xiao Li, Germantown, MD (US); Yongqiang Zhang, Lutherville, MD (US); Kenneth Anthony Kopher, Baltimore, MD (US); John D. Mantlo, Westminster, MD (US); William Alfred Pope, Owings Mills, MD (US); Song Shi, Reisterstown, MD (US); Axel A. Yup, Owings Mills, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 554 days.

(21) Appl. No.: 14/390,596

(22) PCT Filed: Apr. 4, 2013

(86) PCT No.: PCT/US2013/035291
§ 371 (c)(1),
(2) Date: Oct. 3, 2014

(87) PCT Pub. No.: WO2013/152203
PCT Pub. Date: Oct. 10, 2013

(65) Prior Publication Data
US 2015/0118677 A1 Apr. 30, 2015

Related U.S. Application Data

(60) Provisional application No. 61/620,823, filed on Apr. 5, 2012.

(51) Int. Cl.
*C12Q 1/68* (2006.01)
*G01N 1/30* (2006.01)
*C12Q 1/06* (2006.01)
*C12Q 1/04* (2006.01)

(52) U.S. Cl.
CPC .............. *G01N 1/30* (2013.01); *C12Q 1/04* (2013.01); *C12Q 1/06* (2013.01); *G01N 2001/302* (2013.01)

(58) Field of Classification Search
CPC .................................. G01N 1/30; C12Q 1/06
USPC ........................................ 435/6.1, 6.15, 40.5
See application file for complete search history.

(56) References Cited

U.S. PATENT DOCUMENTS

| | | | |
|---|---|---|---|
| 5,436,134 A | 7/1995 | Haugland et al. |
| 5,534,416 A | 7/1996 | Millard et al. |
| 5,891,738 A | 4/1999 | Soini et al. |
| 6,323,337 B1 | 11/2001 | Singer et al. |
| 7,205,100 B2 | 4/2007 | Buttry et al. |
| 9,645,057 B2 * | 5/2017 | Li .............................. G01N 1/30 |
| 2003/0013849 A1 | 1/2003 | Ward et al. |
| 2010/0112682 A1 | 5/2010 | Boyette et al. |

FOREIGN PATENT DOCUMENTS

| | | |
|---|---|---|
| JP | 03215428 B2 | 10/2001 |
| JP | 2012507288 A | 3/2012 |
| WO | 0242267 A2 | 5/2002 |
| WO | 2011124927 A1 | 10/2011 |
| WO | 2011160887 A1 | 12/2011 |

OTHER PUBLICATIONS

Japanese Office Action for Application No. 2015-504727 dated Jan. 24, 2017.
Zipper, Hubert et al., "Investigations on DNA intercalation and surface binding by SYBR Green I, its structure determination and methodological implications," Nucleic Acids Research, Information Retrieval Ltd, Jan. 1, 2004 (Jan. 1, 2004), pp. e103-01, vol. 32, No. 12, XP009140291.
Monis, Paul T., et al., "Comparison of SYTO9 and SYBR Green I for real-time polymerase chain reaction and investigation of the effect of dye concentration on amplification and DNA melting curve analysis", Analytical Biochemistry, Elsevier, May 1, 2005 (May 1, 2005), pp. 24-34, vol. 340, No. 1, XP022593917, Amsterdam, NL.
Gregori G et al, "Resolution of Viable and Membrane-Compromised Bacteria in Freshwater and Marine Waters Based on Analytical Flow Cytometry and Nucleic Acid Double Staining" Applied and Environmental Microbiology, vol. 67(10), 4662-4670; Oct. 2001 (Oct. 2001).
Barbesti S et al. "Two and Three-Color Fluorescence Flow Cytometric Analysis of Immunoidentified Viable Bacteria", Cytometry 40:214-218; 2000.
A. Pianetti et al: "Determination of the 1-9, Viability of Aeromonas hydrophila in 11-15 Different Types of Water by low Cytometry, and Comparison with Classical Methods", Applied and Environmental Microbiology, vo 1 . 71, No. 12, Dec. 1, 2005 (Dec. 1, 2005), pp. 7948-7954, XP55223542, US, ISSN: 0099-2240, DOI: 10.1128/AEM.71.12.7948-7954.2005 * the whole document * * In particular: Abstract; Materials and methods section, flow cytometry and viability staining; Fig. 5; Discussion, last 3 paragraphs. *
M. Berney: "Flow-cytometric study of 1-9, vital cellular functions in *Escherichia* 11-15 *coli* during solar disinfection (SODIS)", Microbiology, vol. 152, No. 6, Jun. 1, 2006 (Jun. 1, 2006), pp. 1719-1729, XP55223549, GBISSN: 1350-0872, DOI: 10.1099/mic. 0.28617-0 * the whole document * * In particular: Abstract; Materials and methods, "flow-cytometric measurements" and "fluorescence stains and their function"; Fig. 5, see legend; Fig. 7, see comparison of Syot 9 alone or in combination with PI *.

(Continued)

*Primary Examiner* — Jezia Riley
(74) *Attorney, Agent, or Firm* — Botos Churchill IP Law LLP

(57) ABSTRACT

Described herein are methods and reagents for identifying and analyzing at least one microorganism (e.g. bacteria) in a sample and reducing the background signal intensity obtained when analyzing the sample by flow cytometry. The sample is prepared by combining the sample with a background signal-reducing molecule or with a nucleic acid stain covalently linked to a quencher. A portion of the particulate matter in the sample can optionally be removed with a resin prior to staining with a nucleic acid stain.

13 Claims, 19 Drawing Sheets

(56) References Cited

OTHER PUBLICATIONS

S. Allegra et al: "Use of Flow Cytometry to Monitor Legionella Viability", Applied and Environmental Microbiology, vol. 74, No. 24, Oct. 10, 2008 (Oct. 10, 2008), pp. 7813-7816, XP55223546, US ISSN: 0099-2240, DOI: 10.1128/AEM.01364-08 * the whole document * * in particular: Title; Abstract; Fig. 1, legend. *

Jung Kyu Choi et al: "3,3'-Diethylthiatricarbocyanine Iodide: A Highly Sensitive Chiroptical Reporter of DNA Helicity and Sequence". International Journal of Molecular Sciences, vo l . 12. No. 12. Nov. 16, 2011 (Nov. 16, 2011), pp. 8052-8062, XP55223668, DOI: 10.3390hms12118052 * the whole document * * In particular: Title; Abstract; p. 8053, chart 1.

Supplementary European Search Report for Application No. 13773119.6 dated Nov. 2, 2015.

Jiaping Tao, et al., Method for eliminating the effect of dead cells in immunofluorescence assay by flow cytometry. Progress in Biochemistry and Biophysics, vol. 17, No. 1, pp. 298-301, Dec. 31, 1990. (English abstract provided).

Hongxing Cai, et al., Raman spectrum study of 3.3'-diethylthiatricarbocyanine iodide. Spectroscopy and Spectral Analysis, vol. 30, No. 12, pp. 3244-3248, Dec. 31, 2010. (English abstract provided).

"Quantitative Analysis of Bacteria in Foods as Sanitary Indicators", Laboratory Guidebook Notice of Change, Effective: Oct. 8, 2010, Revised: Jan. 20, 2011, USDA Website <http://www.fsis.usda.gov/OPHS/rnicroiab/migchp3.pdf>.

Breeuwer et al., "Characterization of uptake and hydrolysis of fluorescein diacetate and carboxyfluorescein diacetate by intracellular esterases in *Saccharomyces cerevisiae*, which result in accumulation of fluorescent product", Applied and Environmental Micriobioly, 61 (4) : 1614-1619 (Apr. 1995).

de Boer et al., "Methology for detection and typing of foodborne microorganisms", International Journal of Food Microbiology, 50(1-2) : 119-130 (Sep. 1999).

Hammes, F. et al., "Cytometric methods for measuring bacteria in water: advantages, pitfalls, and applications", Anal. Bioanal. Chem., vol. 397, pp. 1083-1095 (2010).

International Search Report for Application No. PCT/US2013/035291 dated Jul. 12, 2013.

Quintero-Betancourt et al., "Cryptosporidium parvum and Cyclospora cayetanensis: a review of laboratory methods for detection of the waterborne parasites", Journal of Microbiological Methods, 49(3) : 209-224 (May 2002).

U.S. Appl. No. 61/779,766, filed Mar. 13, 2013.

Barbesti, S. et al, Two and Three-Color Fluorescence Flow Cytometric Analysis of immunoidentified Viable Bacteria, Wiley-Liss, Inc., 2000, pp. 214-218.

\* cited by examiner

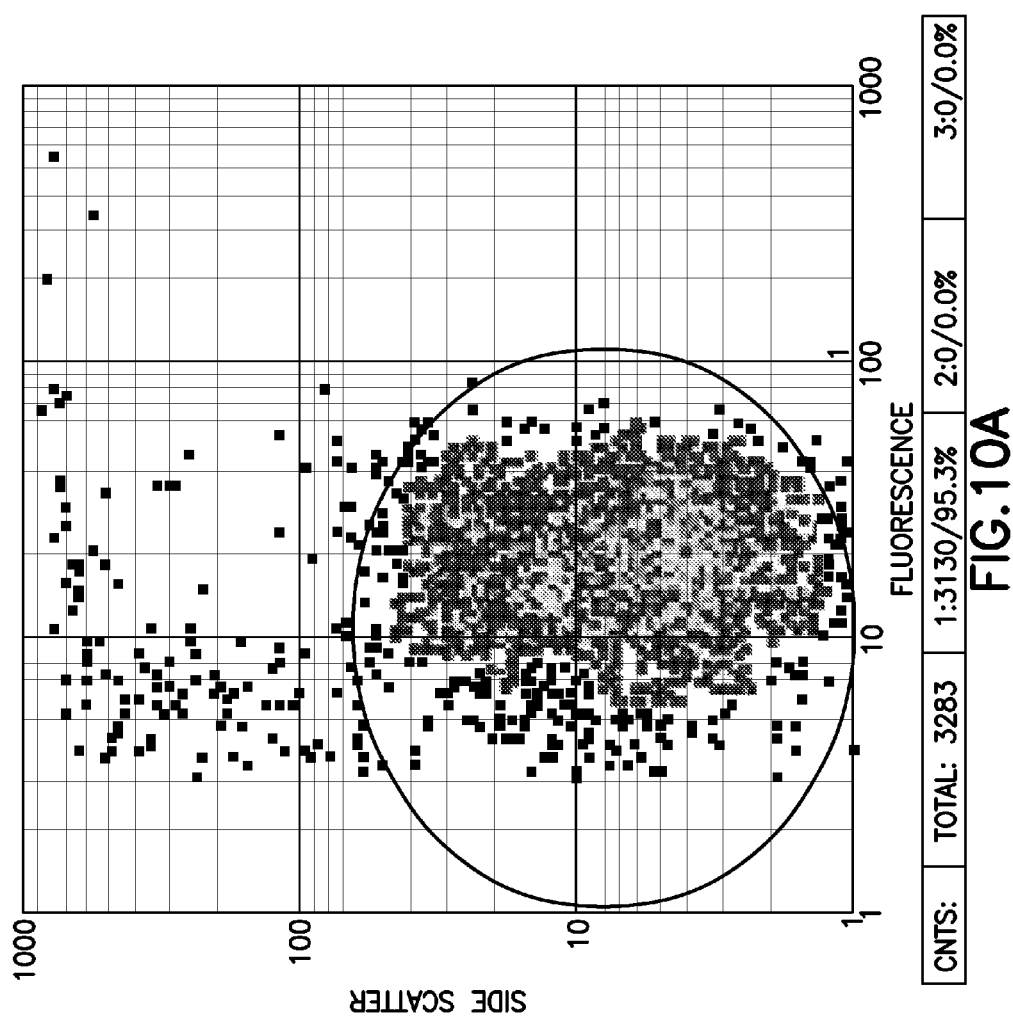

SAMPLE PREPARATION FOR FLOW CYTOMETRY

CROSS REFERENCE TO RELATED APPLICATIONS

The present application is a national phase entry under 35 U.S.C. § 371 of International Application No. PCT/US2013/035291 filed Apr. 4, 2013, published in English, which claims the benefit of the filing date of U.S. Provisional Patent Application No. 61/620,823, filed Apr. 5, 2012, and is related to U.S. Provisional Application No. 61/779,766 filed Mar. 13, 2013, which is commonly owned with the present application, the disclosures of which are hereby incorporated herein by reference.

BACKGROUND OF THE INVENTION

Determining the identity and total number of viable organisms in a particular sample is of tremendous importance. Of specific importance is monitoring and ensuring the safety of food and water supplies through the surveillance and identification of pathogenic organisms in foods and in the environment quickly, efficiently, and accurately.

One such method to accomplish this is the total viable organism (TVO) assay. The TVO assay is widely used today as a quality control application in the industrial microbiology field. The TVO assay is used, for example, to monitor the number and types of bacteria in consumer food products, such as meat. The TVO method can also be used to monitor bacterial populations in drinking water. Monitoring for food and water is, of course, critical to ensure that the food and water supply is safe for consumption.

The steps of the TVO assay generally include: 1) obtaining a test sample; and 2) culturing or plating the sample on agar (a gelatinous nutrient substance), placed in a suitable container. The microbial organisms are allowed to grow and the colony forming units (CFUs) are calculated based on the number of colonies that form on the agar. CFUs can be calculated only after allowing time for colony growth. Samples are typically diluted and this dilution factor (i.e., volume ratio of sample to total volume) is taken into account when calculating CFUs.

Samples can also be cultured on a variety of agar plates that contain different types of selective media to help isolate target microorganisms and more accurately and reliably determine what types of microorganisms are present. Selective agents (e.g., antibiotics, anti-fungals, etc.) will eliminate certain non-target microorganisms (e.g., bacteria of no interest). This avoids the possibility of spurious results that might occur if colonies from many different types of microorganisms are formed.

Selective agents can also favor the growth of certain types of microorganisms over others. Although the TVO assay allows for detection of different microorganism species, e.g., different bacterial species, food and environmental microbiologists must often choose between enumeration and identification without the option of both. Although selective agents can be added to favor the growth of a specific group of organisms, the TVO assay is often based on the ability of normal healthy cells to multiply in nutrient-rich medium (i.e., without selection). TVO therefore has the capacity to measure the total number of microorganisms or a group of microorganisms in the sample tested. However, because of the lack of ability to differentiate specific microorganisms, TVO can be relatively nonspecific for the microorganism population as a whole.

There are numerous other methods available that identify specific microorganisms, especially pathogens. Such methods are widely used in the clinical setting. Methods for detecting microorganisms often depend upon enrichment of the microorganism culture in order to increase the numbers of the target microorganism and to allow for the resuscitation of injured microorganisms. When selective and differential plating is employed, researchers are able to discriminate the target organism from the background microflora. However, the results are almost always non-enumerative. In other words, only the presence or absence of a particular bacterial population can be determined, not the quantity.

Utilizing both sample enrichment and selective plating results is a time-consuming assay, which often takes several days before even a preliminary result can be obtained. Although such enrichment and selective plating is a staple procedure to determine the number and types of microorganisms in a sample, it can typically take several days to get a final result after colonies grown on agar are counted. The amount of time it takes to obtain results is the most significant drawback of using the staple TVO assay.

Different methods have been developed that attempt to shorten detection time by eliminating the selective and differential plating steps. Such methods include DNA hybridization, agglutination, and enzyme immunoassay. Although these alternative techniques have shortened the time for detection, culture enrichment steps remain necessary because these methods only allow for the ultimate detection of $10^3$-$10^4$ CFU of the target pathogen. Therefore, confirmation for presumptively positive results remains necessary for the TVO assay.

Furthermore, there is no universal method or single technique available for analyzing a biological sample, especially a food sample, to detect for the presence or absence of multiple microorganisms. This makes the sample preparation steps for the separation and subsequent concentration of microorganisms from a biological sample prior to assay for the microorganisms a rate limiting step in molecular methods for the detection of pathogens, including foodborne pathogens.

With regard to specific sample preparation techniques for separation of microorganisms, techniques that utilize centrifugation followed by washing and filtration steps are not advantageous because they result in a significant loss of, or damage to, microorganisms during the processing. Furthermore, the whole procedure is not amenable for automation.

In order to achieve separation of the microorganism from the sample, affinity agents for a particular microorganism have been employed. However, affinity agents used to isolate microorganisms from the complex matrices are also complicated to deploy because of: 1) lack of universal affinity agents that bind to all organisms selectively from the other sample constituents; 2) variability in binding affinities of different organisms to the universal affinity reagents; and 3) difficulty in eluting the bound organism back into the solution.

Other techniques for identifying pathogens in food and water are also known. For example, flow cytometry has been reported as a rapid technique for enumerating and identifying microorganisms. Flow cytometry is a method originally used to separate and analyze eukaryotic cell populations but has been employed in the evaluation and detection of microorganisms, as well. Specifically, microorganisms that have been fluorescently stained, for example with a nucleic acid dye, are passed through a beam of light. A pattern unique to the microorganism of interest is achieved by the combination of both the adsorption and scattering of the light. (Breeuwer et al., Characterization of uptake and hydrolysis of fluorescein diacetate and carboxyfluorescein diacetate by intracellular esterases in *S. cerevisiae*, which result in accumulation of fluorescent product, *Appl. Environ. Micriobiol.*, 61(4):1614-9 (April 1995); de Boer & Beumer, Methodology for detection and typing of foodborne microorganisms, *Int. J. Food. Microbiol.*, 50(1-2):119-30 (September 1999)).

The main advantage of flow cytometry is that it is fast and easy to perform. Flow cytometry is adaptable to different types of samples and methods, making it a robust application that is also amenable to automation. It is no surprise that numerous flow cytometry applications have emerged in industrial biotechnology, food and pharmaceutical quality control, routine monitoring of drinking water and wastewater systems, and microbial ecological research in soils and natural aquatic habitats. Flow cytometry results correlate well with the results of standard plate counting methods.

However, flow cytometry has other limitations, such as the need to dye label target microorganisms for detection, the high cost of the equipment and the need for specialized training of personnel. Further limits on detection are imposed by interference of nonspecific fluorescence, less than optimal detection limits, difficulty in applying the method to solid or particulate food samples, the inability to differentiate between viable and dead cells unless specialized staining is used, and destruction of cellular viability that may also occur during sample processing (Quintero-Betancourt et al., *Cryptosporidium parvum* and *Cyclospora cayetanensis*: a review of laboratory methods for detection of the waterborne parasites, *J. Microbiol. Methods*, 49(3):209-24 (May 2002)). The extensive and routine use of this technique has begun to alleviate these drawbacks.

Other practical problems remain with flow cytometry, especially in the context of analyzing biological or environmental samples derived from what are referred to as "complex matrices." Complex matrices may consist of substances, including particulate matter, which interferes with the detection of microorganisms in the biological or environmental sample. The nucleic acid dyes, used to detect the microorganism in the sample, may non-specifically bind to such particulate matter in the sample matrix resulting in a high background fluorescent signal. This high background makes it difficult to identify and analyze low concentrations of microorganism in the sample.

As described in U.S. Pat. No. 7,205,100 to Buttry et al., the entire contents of which are hereby incorporated by reference herein, fluorescent background and fluorescent signals generated by membrane permeable dead cells can be reduced by mixing target specific fluorescent dyes and fluorescence quenchers in the samples of interest. However, in some sample matrices containing extracellular particles that have non-specific affinity to the target specific fluorescent dyes, fluorescent background cannot be quenched effectively by fluorescent quenchers. In addition, in samples containing large amount of extracellular particles that have non-specific affinity to the target specific fluorescent dyes, the vast majority of target specific dyes will bind to the particles non-specifically, and as a result not enough dye molecules are available in the solution to label the target organisms.

Consequently, methods that address the drawbacks in current methods for detecting the presence or absence of microorganisms in a sample using flow cytometry are sought.

BRIEF SUMMARY OF THE INVENTION

The present invention relates to a method of identifying the presence or absence of at least one microorganism in a sample. As described herein, a sample to be tested for the presence or absence of at least one microorganism is first obtained and then prepared for the assay to be performed. Fluorescent nucleic acid stains permeable to both live and dead organisms are used to label cells in suspension for flow cytometry studies. However, detection sensitivity of such flow cytometry studies can be adversely affected while the targeted cells are in a suspension with the particulate matter from the sample matrix that binds to the nucleic acid dyes non-specifically. Several approaches are described herein to mask and/or remove the fluorescent signals from those interfering particles in the solution and subsequently increase detection sensitivity.

In one embodiment, a method of analyzing a sample to determine the amount of viable microorganisms includes obtaining a sample and preparing the sample for an assay to detect the presence or absence of viable microorganisms in the sample. In one embodiment, the assay is a TVO assay. As part of the sample preparation, excess amounts of a background signal-reducing molecule are added to the sample. The background signal-reducing molecule does not permeate viable cells in the sample but has similar binding properties to non-viable cells (e.g., dead cells, cell debris) and other non-cellular matter in the sample in the prepared sample as a nucleic acid stain that permeates viable cells (which is also added to the sample). The prepared sample is then assayed for total viable organisms.

Examples of background signal-reducing molecules contemplated herein are hemicyanines or closed chain cyanines. Such molecules include the basic cyanine structure having the five-membered heterocyclic ring containing at least one nitrogen atom. The basic cyanine structure is illustrated as Structure (I):

Structure (I), or a salt thereof,
wherein, Y is:

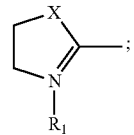

n is 0 or an integer up to about 5; in some embodiments n is 0 or an integer up to about 3;

X is either carbon or sulfur; and $R_1$ is optionally hydrogen, an alkyl group having from 1-6 carbon atoms, a sulfite moiety or an alkyl amide. In certain embodiments $R_1$ is selected to decrease cell permeability of the background-signal reducing molecule into the viable target microorganism.

Z is either the same or different from Y. Whether the same or different, Z also includes the five-membered heterocyclic ring of Y. If Z is different from Y, the difference is in the substituents of the five-membered heterocyclic ring.

Optionally, the Y moiety has a benzene or benzene derivative fused thereto. The benzene or benzene derivative can be substituted or unsubstituted. Benzene derivatives, as used herein, include polycyclic aromatic moieties such as naphthalene. In other embodiments the five-membered ring structure has a quinolone substituent. The quinolone substituent can also be substituted or unsubstituted.

In another embodiment, a method of analyzing a sample to determine the amount of viable microorganisms includes obtaining a sample and preparing the sample for a TVO assay. A nucleic acid stain that is covalently linked to a fluorescent quencher that does not permeate viable cells is added to the sample. A nucleic acid stain that permeates viable cells and that is not covalently linked to a fluorescent quencher is also added to the sample. The nucleic acid stain that does not permeate viable cells can quench the fluorescent signal of the nucleic acid dye by spectra overlap.

In yet another embodiment, the preparation of the sample for the TVO assay includes removal of at least part of the particulate matter from the complex matrix with the use of a resin. In one embodiment, the removal of at least part of the particulate matter from the complex matrix with a resin includes obtaining a sample and combining the sample with a resin. The resin is subsequently removed from the sample carrying at least a portion of the particulate matter from the sample. To the sample is added a nucleic acid stain that permeates viable cells. The prepared sample is then assayed for the presence and amount of total viable organisms. In one embodiment, the removal of particulate matter with a resin can be employed prior to adding excess amounts of a background signal-reducing molecule, or prior to adding a nucleic acid stain that is covalently linked to a fluorescent quencher.

A further embodiment of the invention includes a commercial kit for the detection of at least one microorganism in a sample comprising at least one of a background signal-reducing molecule or a nucleic acid covalently linked to a quencher; a nucleic acid stain; and optionally, a resin. The commercial set is combined with the sample and subjected to an assay that will determine the presence or absence of viable microorganisms in the sample.

BRIEF DESCRIPTION OF THE DRAWINGS

FIGS. 10A and 10B show an intensity plot for a flow cytometry analysis reporting the concentration of viable organisms where approximately 15,000 cfu/ml of E. coli was spiked in the water sample with or without 5 μM Propidium Iodide added to the water sample.

DETAILED DESCRIPTION

Figure 1A:
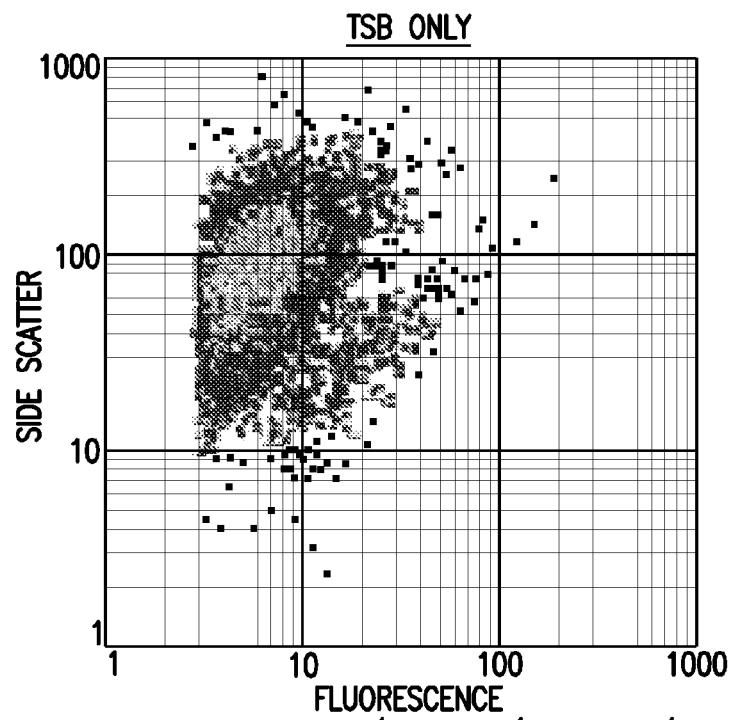
FIGS. 1A-1C report the amount of background signal in samples treated with or without Molecule of Formula (II).

Described herein are methods for improving upon known assays, such as the TVO assay, by deploying flow cytometry for sample analysis. Samples obtained from food products, cosmetics, and soil samples, can be difficult to accurately analyze using flow cytometry because of the interference caused by the particulate matter in "complex matrices." Complex matrices, as used herein, are samples with significant amounts of material extraneous to the assay. For the assays contemplated herein, these extraneous materials are dead cells, cellular debris and other sample constituents other than viable microorganisms. The methods described herein aid in improving sample preparation in a manner necessary to detect low levels of pathogens or sporadic contamination, which may perhaps reduce or even eliminate the need to enrich the sample culture prior to assay.

Specifically, the methods and molecules described herein improve sample quality prior to subjecting the sample suspected of containing target microorganisms to tests or assays for the detection of the presence or absence of target microorganisms. Advantages of using the methods described herein include, but are not limited to, facilitating the detection of multiple microorganism strains; removing matrix-associated assay inhibitors; removing interfering matrix particulates; enhancing the detection signal strength or ability to read the detection signal and reducing requisite sample size to allow for the use of food sample sizes more representative of serving size and/or small media volumes.

The methods and reagents described herein for sample preparation facilitate the detection of low levels of pathogens or sporadic contamination. The methods and reagents reduce or even eliminate the need to enrich the sample culture to increase the amount of microorganisms available for detection or in order to accelerate microorganism growth prior to sample assay.

The methods and molecules described herein concentrate the target microorganisms/pathogens/bacteria in the sample (if present) by removing matrix-associated inhibitors from the sample that may interfere with the assay for the target microorganisms/pathogens/bacteria. The methods and molecules described herein also enhance the signal to noise ratio obtained from the sample that is indicative of the presence or absence of the target microorganisms/pathogens/bacteria. The described methods are advantageous because they are universal (e.g., applicable to multiple types of matrices and target microorganisms/pathogens/bacteria). The described methods are simple, rapid, and inexpensive. Furthermore, the methods described herein reduce the chance for false positive or negative results that might occur because of cross-reactivity of the detection dyes added to the sample with both the target microorganisms/pathogens/bacteria and the residual matrix components or dead target cells.

Excess Background Signal-Reducing Molecule

In one embodiment, the method of analyzing a sample for the amount of viable microorganisms (TVO) includes the steps of i) obtaining the sample; ii) preparing the sample by adding excess amounts of a background signal-reducing molecule; and by adding a nucleic acid stain that permeates viable cells. The background signal-reducing molecule does not permeate viable cells but has similar binding properties as the nucleic acid stains to the prepared sample. The prepared sample is then analyzed.

The methods described herein contemplate obtaining a sample. The sample may be, for example, an environmental sample, a food sample, a cosmetic sample, or a biological sample. These types of samples are often in the form of a complex matrix containing various particulate matter such as soil debris extracellular matrix, etc.

The sample to be analyzed is prepared using known techniques for the particular type of sample to be analyzed and are well known to the skilled artisan. As such sample preparation techniques are not described in detail herein. In one exemplary embodiment, the process for preparing a meat sample includes first blending the meat with a buffer. The use of a standard protocol for blending meat with the proper buffer to obtain the meat extract is contemplated as suitable for use in the methods described herein. Blending is accomplished using a variety of techniques, such as adding the meat sample to the appropriate volume of phosphate buffered dilution water and transferring to a stomacher bag (<50 μM filter—Interscience Bag system: 111625 or equivalent) and blended in a stomacher for (e.g., Tekmar (Seward) Stomacher Lab Blender 400 or equivalent). Such protocols are well known to those skilled in the art and are not described in detail herein. Examples of such protocols are described on the USDA website (http://www.fsis.usda.gov/OPHS/microiab/mlgchp3.pdf), which is incorporated by reference herein.

After the sample is prepared an excess amount of a background signal-reducing molecule that does not permeate viable cells but has similar binding properties as the nucleic acid stains is added to the prepared sample. Since the background signal-reducing molecule is not permeable to the viable cells, only the cell permeable nucleic acid dye can label the viable cells and generate fluorescent signals from the cells. Interfering particles that bind to the dye non-specifically are bound to both the nucleic acid stain and the molecule described herein. The background signal-reducing molecule can compete for the binding of the nucleic acid stains with the particulate matter in the matrix, such as extra cellular particles and dead cells, and as a result reduce the fluorescent signal caused by the non-specific binding of the nucleic acid stains when samples are analyzed by flow cytometry.

The amount of background signal-reducing molecule is not limited so long as the amount is in excess of the nucleic acid stain so as to favorably compete with the nucleic acid stain with regard to binding substantially all of the particulate matter in a complex matrix sample. Because the excess amount of background signal-reducing molecule can favorably compete with the nucleic acid stain and bind to the particulate matter in the sample, non-specific binding of the nucleic acid stain to the particulate matter is reduced, decreasing non-specific fluorescent intensity. As such, "excess concentrations" as described herein are qualitative and relative to the amount of nucleic acid dye added to the sample. The skilled person can readily determine the amount of background signal-reducing molecules to be added to mitigate, reduce or eliminate the undesired non-specific binding of the nucleic acid dye to non-target particles for a particular application.

In one embodiment, the concentration of background signal-reducing molecule is about 0.1 μM to about 50 μM when combined with the sample. In another embodiment, the concentration of background signal-reducing molecule is about 0.1 μM to about 10 μM when combined with the sample. In yet another embodiment, the concentration of background signal-reducing molecule is about 0.5 μM to about 5 μM when combined with the sample.

In one embodiment, an excess amount of the background signal-reducing molecule that does not permeate viable cells but has similar binding properties as the nucleic acid stains is added sequentially or simultaneously with the cell-permeable nucleic acid stain to the sample to be analyzed. In another embodiment, the background signal-reducing molecule is added prior to the addition of the nucleic acid stain.

After the addition of the background signal-reducing molecule to the sample, the mixture can be incubated. In one embodiment, the mixture is incubated for about 2 minutes to about 1 hour. In another embodiment, the mixture is incubated for about 2 minutes to about 30 minutes. In yet another embodiment, the mixture is incubated for about 2 minutes to about 5 minutes.

The structure of the background signal-reducing molecule is not limited so long as the molecule can bind to particulate matter in a complex matrix sample, reduce background fluorescent signal when analyzed by flow cytometry, and does not significantly permeate viable microbial cells. Modifications to the chemical structure of the background signal-reducing molecule to reduce cell permeability, including for example, adding charged molecules such as Acid Black 48 and trypan blue to the molecule, are known to those skilled in the art and not described in detail herein.

In one embodiment, a quencher is attached to the background signal-reducing molecule. The background signal-reducing molecule, with quencher attached, will attach to the binding sites of the background signal-reducing molecule. The quencher will quench the fluorescent signal of any nucleic acid dye, sufficiently proximate thereto, that non-specifically binds to the particulate matter in the sample. The presence of background signal-reducing molecules with quenches attached thereto further reduces background signal in a two-fold manner: i) by taking up binding sites on non-target substances in the sample; and ii) by quenching signal from any target dye that binds to non-target substances in the sample. The choice of quencher depends on the type of nucleic acid dye used to detect and analyze the microbial cells, and may include, for example trypan blue and crystal violet. Fluorescent quenchers are well known to those skilled in the art and are therefore not described in detail herein.

Examples of background signal-reducing molecules contemplated herein are hemicyanines or closed chain cyanines. Such molecules include the basic cyanine structure having the five-membered heterocyclic ring containing at least one nitrogen atom. The basic cyanine structure is illustrated as Structure (I):

Structure (I), or a salt thereof,
wherein, Y is:

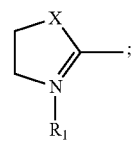

n is 0 or an integer up to about 5; in some embodiments n is 0 or an integer up to about 3;

X is either carbon or sulfur; and $R_1$ is optionally hydrogen, an alkyl group having from 1-6 carbon atoms, a sulfite moiety or an alkyl amide. In certain embodiments $R_1$ is selected to decrease cell permeability of the background-signal reducing molecule into the viable target microorganism.

Z is either the same or different from Y. Whether the same or different, Z also includes the five-membered heterocyclic ring of Y. If Z is different from Y, the difference is in the substituents of the five-membered heterocyclic ring.

Optionally, the Y moiety has a benzene or benzene derivative fused thereto. The benzene or benzene derivative can be substituted or unsubstituted. Benzene derivatives, as used herein, include polycyclic aromatic moieties such as naphthalene. In other embodiments the five-membered ring structure has a quinolone substituent. The quinolone substituent can also be substituted or unsubstituted.

In one embodiment, the background signal-reducing molecule includes a compound of Structure (I), wherein n is up to 3, X is sulfur, $R_1$ is an alkyl amide, and Y has a benzene moiety or benzene moiety derivative fused thereto.

In one embodiment, the background signal-reducing molecule includes at least one of the following:

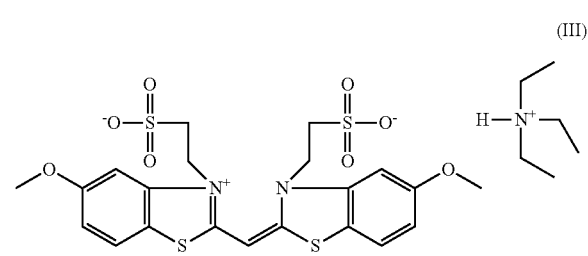

(I)

(Commercially available from Sigma-Aldrich®, catalog No. 381306);

(II)

(Commercially available from Sigma-Aldrich®, catalog No. S992003);

(III)

(Commercially available from Sigma-Aldrich®, catalog No. S981826);

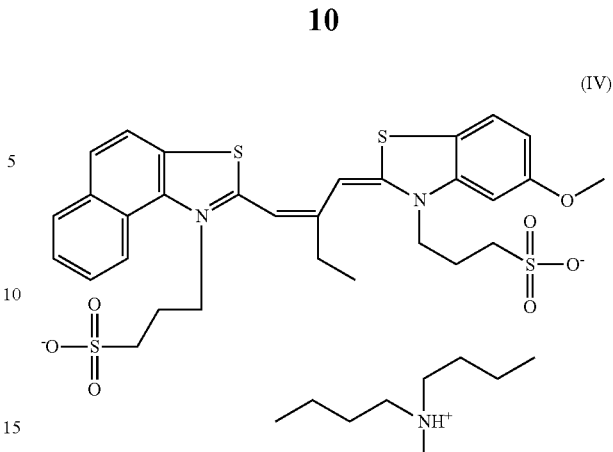

(IV)

(Commercially available from Sigma-Aldrich®, catalog No. S171360);

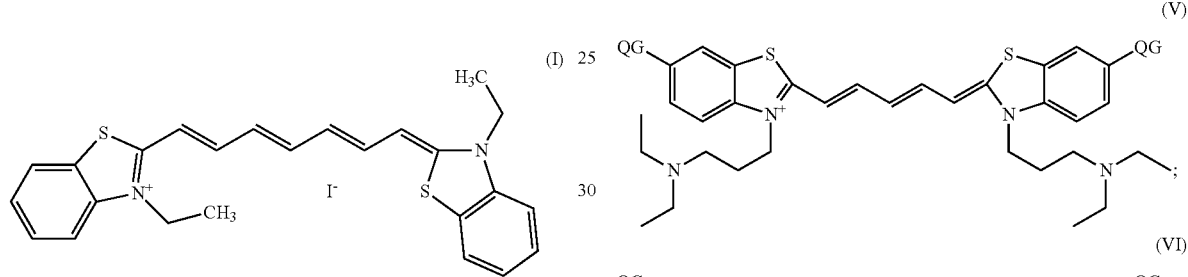

(V)

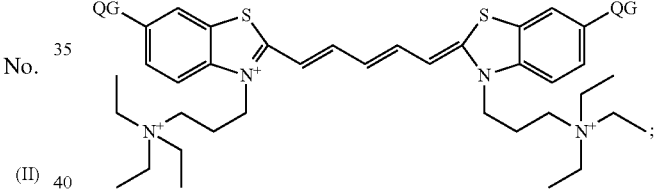

(VI)

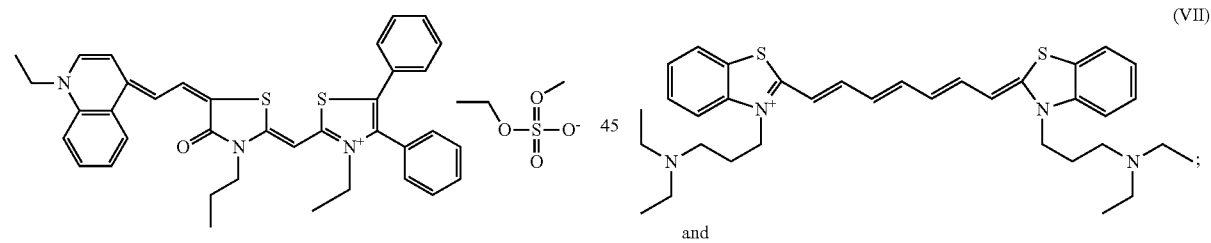

(VII)

and

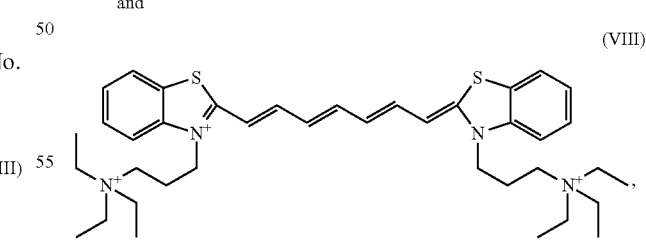

(VIII)

wherein QG represents a fluorescent signal quenching group.

In order to detect for the presence of microorganism in the sample a nucleic acid stain is added to the sample. Such stains, for example SYTO® 13 by Invitrogen, are well known to one skilled in the art. When selecting a stain, the skilled person will consider the following factors: i) the target microorganism of interest (e.g., gram positive or gram negative), the downstream assay being deployed for determining the presence or absence of the microorganism in the sample; and iii) the contrast between the selected stain and other stains for sample constituents. The skilled person is aware of other considerations when selecting a dye stain for the method described herein. The nucleic acid stain can be added simultaneously with or after the incubation with a background signal-reducing molecule.

After staining with a nucleic acid stain, the sample is then analyzed for the presence or absence of target microorganisms using flow cytometry. The use of flow cytometry is well known to those skilled in the art, and not described herein. A description of flow cytometry analysis is described in Hammes, F. et al., "Cytometric methods for measuring bacteria in water: advantages, pitfalls, and applications," Anal. Bioanal. Chem., Vol. 397, pp. 1083-1095 (2010), which is incorporated herein by reference. The whole process can be automated as well. The described method adapts the sample preparation protocol for flow cytometry to include the addition of substances that improve the signal to background ratio for target substances (e.g., viable microorganisms) in the sample.

The methods and molecules described herein reduce background signal intensity obtained when the nucleic acid stains non-specifically bind to particulate matter in a sample containing a complex matrix. The reduction in background signal intensity is compared to what the background signal intensity would be for an identical sample to which the molecules and resins described herein have not been added. In one embodiment, the background signal intensity is reduced by at least about 90%. In another embodiment, the background signal intensity is reduced by at least about 70%. In yet another embodiment, the background signal intensity is reduced by at least about 50%.

Quencher Covalently Linked to Nucleic Acid Dye

In one embodiment, a method of analyzing a sample to determine the amount of viable microorganisms includes: i) obtaining a sample; ii) preparing the sample; iii) adding a nucleic acid stain that is covalently linked to a fluorescent quencher; iv) adding a nucleic acid stain that does not contain a quencher and that permeates viable cells; and (v) analyzing the prepared sample.

In this embodiment, some of the nucleic acid stain is covalently linked to a fluorescent quencher that does not permit the stain to permeate viable cells and can quench the fluorescent signal of the nucleic acid stain by spectra overlap. Since the nucleic acid stain with quencher is not permeable to the viable cells, only the cell permeable nucleic acid stain without the quencher can label the viable cells. Particulate matter such as dead cells or other interfering particles that can bind non-specifically to nucleic acid stains take up both the nucleic acid stain with a quencher and the nucleic acid stain without a quencher. The stain-quencher molecule competes for the binding sites on the particulate matter with the dye that does not have a quencher bound thereto. The binding of the stain-quencher molecule to the particulate matter reduces the intensity of the fluorescent signals that would otherwise be emitted by the nucleic acid stains taken up by the particulate matter.

In one embodiment, an excess amount of the nucleic acid stain with quencher is added sequentially or simultaneously with the cell permeable nucleic acid stain without quencher to the sample to be analyzed. In another embodiment, the nucleic acid stain with quencher is added prior to the addition of the nucleic acid stain without quencher. In this embodiment, the nucleic acid stain without quencher does not compete with the nucleic acid stain with quencher for the binding sites on the particulate matter.

Removing Particulate Matter with a Resin

In one embodiment, the preparation of the biological sample includes removal of at least portion of the particulate matter from the complex matrix with the use of a resin prior to analysis. Methods for removal of at least portion of the particulate matter are described in U.S. application Ser. No. 61/779,766, filed Mar. 13, 2013, incorporated by reference in its entirety herein, and commonly owned with the present application. Briefly, the methods and reagents described in U.S. Application No. 61/779,766 separate microorganisms in a sample from other sample constituents that are commonly described as possessing complex matrices (e.g., ground beef, eggs, milk, soil, cosmetics, etc.) and enhance sample quality prior to subjecting the sample suspected of containing target microorganisms to tests or assays for the detection of the presence or absence or quantity of target microorganisms. In another embodiment of the invention, resins are used to modulate or reduce the interference of the complex matrices with downstream sample assay analysis.

Various resins are known in the art and selection of a particular resin or resins will depend on the nature of the biological or environmental sample to be analyzed. The resin can be removed prior to performing the assay by techniques such as filtration, but the particular technique employed is largely a matter of design choice and depends upon the type of resin and sample preparation. The skilled person will select a suitable separation technique based upon these and other factors. In one embodiment, non-functional resins, such as the XAD resins manufactured by Rohm & Haas, particularly XAD-4 resin, which is a non-functional copolymer of styrene and divinyl benzene, may be used in the practice of the described methods.

In one embodiment, the sample, after resin treatment and removal of resin, is analyzed using a flow cytometer. An appropriate stain, such as a nucleic acid stain or other fluorescent dye, is combined with the sample after removal of resin and prior to flow cytometry. The dye facilitates the detection of the assay target in the flow cytometer. Enhancing techniques, such as quenching, may also be employed to further improve the integrity of the assay.

The removal of particulate matter with a resin can be employed alone in preparing the sample for staining with a nucleic acid stain or may be used in combination with the various methods and molecules described herein. For example, the removal of particulate matter with a resin can be completed prior to adding an excess amount of a background signal-reducing molecule described herein or prior to adding a nucleic acid stain covalently linked to a quencher, also described herein.

In one embodiment, the removal of at least part of the particulate matter from the complex matrix with a resin includes: i) obtaining a sample; ii) combining the sample with a resin; iii) removing the resin to which at least a portion of the particulate matter is adhered from the sample; iv) adding an excess amount of a background signal-reducing molecule; v) adding a nucleic acid stain that permeates viable cells, and vi) analyzing the biological sample.

In another embodiment, the removal of at least part of the particulate matter from the complex matrix with a resin includes: i) obtaining a sample; ii) combining the sample with a resin; iii) removing the resin to which at least a portion of the particulate matter is adhered from the sample; iv) adding a nucleic acid stain covalently linked to a quencher; v) adding a nucleic acid stain that permeates viable cells; and vi) assaying the prepared sample for the presence, absence, or quantity of viable microorganisms in the sample.

Kits

A further embodiment of the invention includes a commercial kit for the detection of at least one microorganism in a sample comprising at least one of a background signal-reducing molecule or a nucleic acid covalently linked to a quencher; a nucleic acid stain; and optionally, a resin.

The following examples are provided to further illustrate certain embodiments of the invention. As such, the examples are not limiting in terms of materials, compositions and conditions used. Other suitable modifications and adaption of the variety of conditions and parameters normally encountered and that are obvious to those skilled in the art are within the spirit and scope of the invention described herein.

EXAMPLES

As discussed above, nucleic acid stains, used to detect and analyze for the presence of microorganism in a sample, can non-specifically bind to particulate matter in samples containing a complex matrix, causing high background signal intensity. Examples 1-9 that follow are designed to demonstrate the efficacy of the various background signal-reducing molecules described herein for reducing background signal intensity in a complex matrix when analyzed by flow cytometry. In each of Examples 1-9, a complex matrix is used, (e.g., trypticase soy broth, process water, swab samples) containing various types of particulate matter, to which a background signal-reducing molecule is added. For comparison, a control sample is prepared with the sample matrix only, without the addition of a background signal-reducing molecule. A nucleic acid stain is then added to each of the samples. The samples are then analyzed by flow cytometry to determine if the background signal-reducing molecule reduces background signal intensity caused by non-specific binding of the nucleic acid stain to the particulate matter in the sample matrix. Because flow cytometry is designed to only detect fluorescent signal that is bound to a particle or cell, any residual fluorescent signal from the background signal-reducing molecule and nucleic acid stain that remains in solution will not be detected.

In Example 10, the same general procedure described above for Examples 1-9 is employed, however, bacteria was spiked into the sample matrix. This Example was designed to demonstrate that the background signal-reducing molecules not only reduce background signal intensity but also do not interfere with the detection of viable microorganism in the sample. Examples 1-10 are discussed in detail below.

Example 1

Figure 1B:
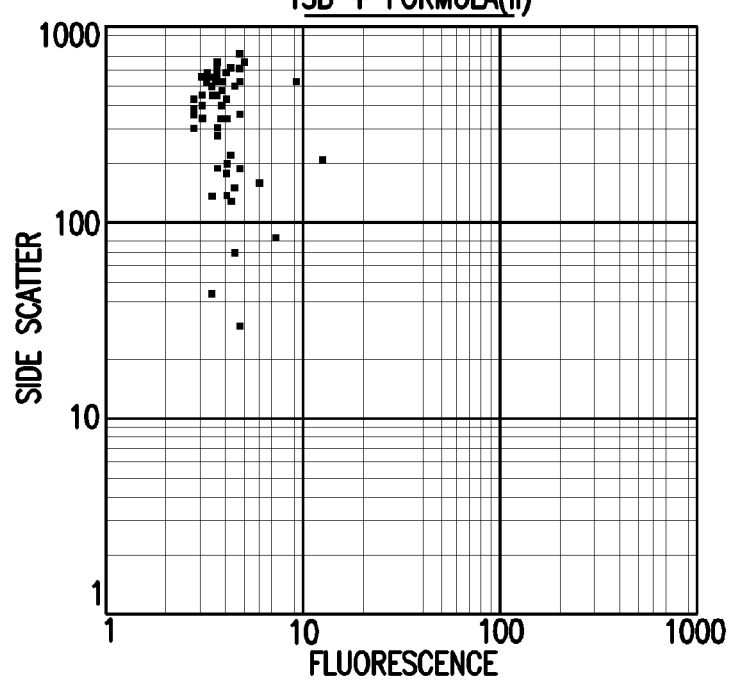
Figure 1C:
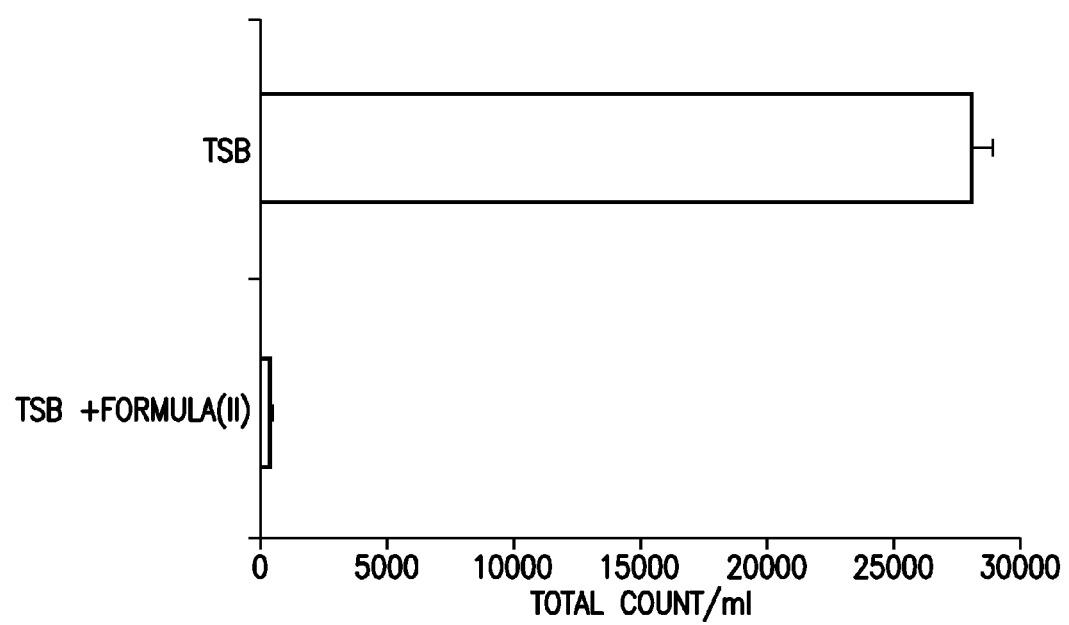

Molecule of Formula (II) was added to trypticase soy broth (TSB) to make a final concentration of 5 µM. The mixture was incubated for 30 minutes prior to the addition of nucleic acid stain Syto® 62 at 0.2 µM final concentration. The mixture was analyzed by flow cytometry. As a control, a sample containing only TSB and nucleic acid stain and not Molecule of Formula (II) was also tested. The results are summarized in FIGS. 1A-1C and demonstrate that background signal is reduced from 6591 counts in the TSB only sample to 58 counts in the sample mixed with Molecule of Formula (II). This demonstrates that background signal (that is, signal from dye bound to sample particulate) is reduced by approximately 99%.

Example 2

Figure 2A:
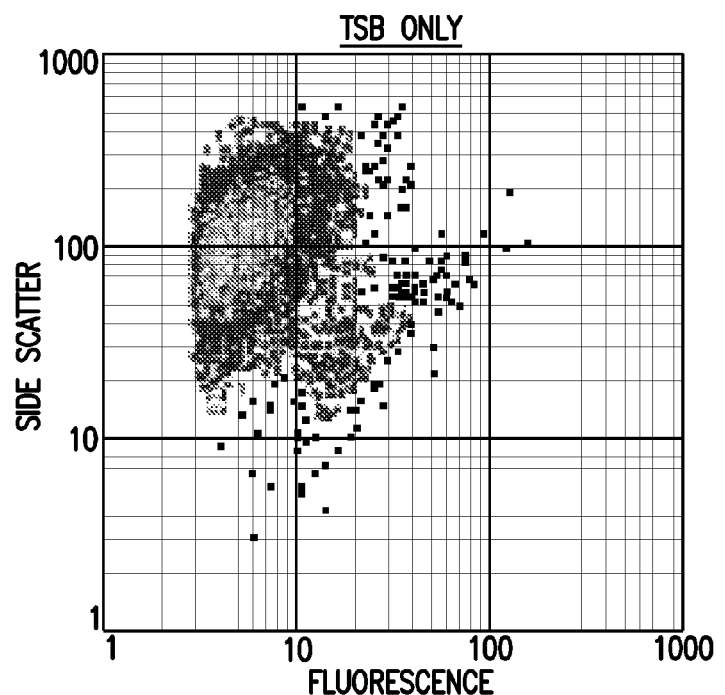
FIGS. 2A-2C report the amount of background signal in samples treated with or without Molecule of Formula (II) added prior to or simultaneously with a nucleic acid stain.
Figure 2B:
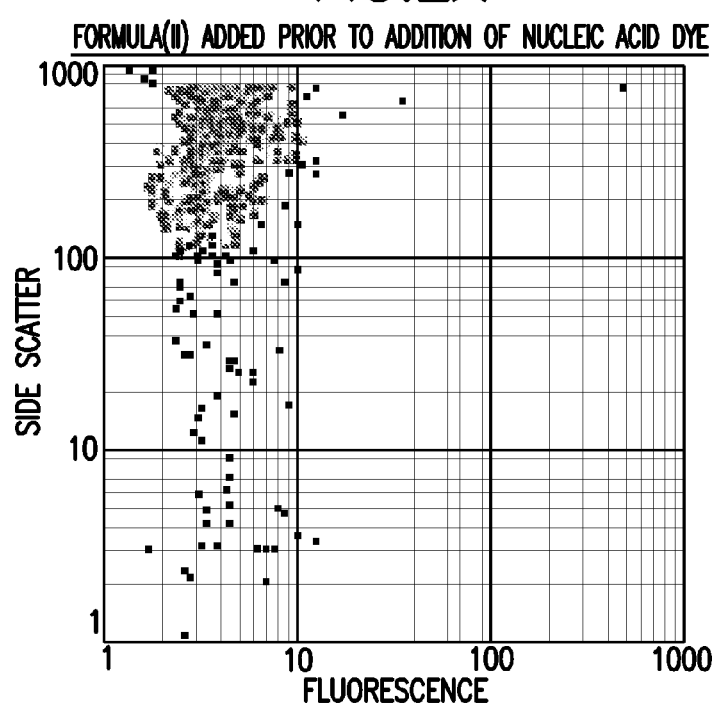
Figure 2C:
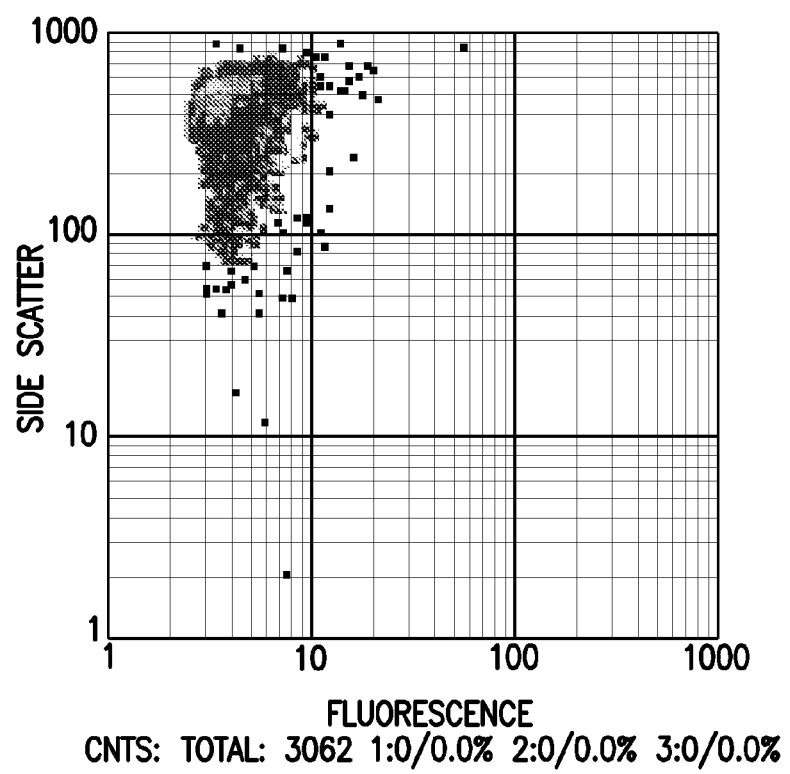

Molecule of Formula (II) was added to TSB to make a final concentration of 5 µM in the TSB. The mixture was either incubated for 5 minutes prior to the addition of nucleic acid stain Syto® 62 at 0.2 µM final concentration or added simultaneously with the nucleic acid stain without pre-incubation. The mixtures were analyzed by flow cytometry. As a control, a sample containing only TSB and nucleic acid stain and not Molecule of Formula (II) was also tested. The results are summarized in FIGS. 2A-2C and demonstrate that the background signal is reduced from 6436 counts in the TSB with nucleic acid stain only to 3062 counts in the TSB mixed simultaneously with Molecule of Formula (II) and stain. This demonstrates a reduction of background signal by approximately 51%. However, when Molecule of Formula (II) is mixed and incubated with the TSB prior to the addition of nucleic acid stain, the background signal is reduced to 486 counts, almost 92% reduction in background signal.

Example 3

Figure 3:
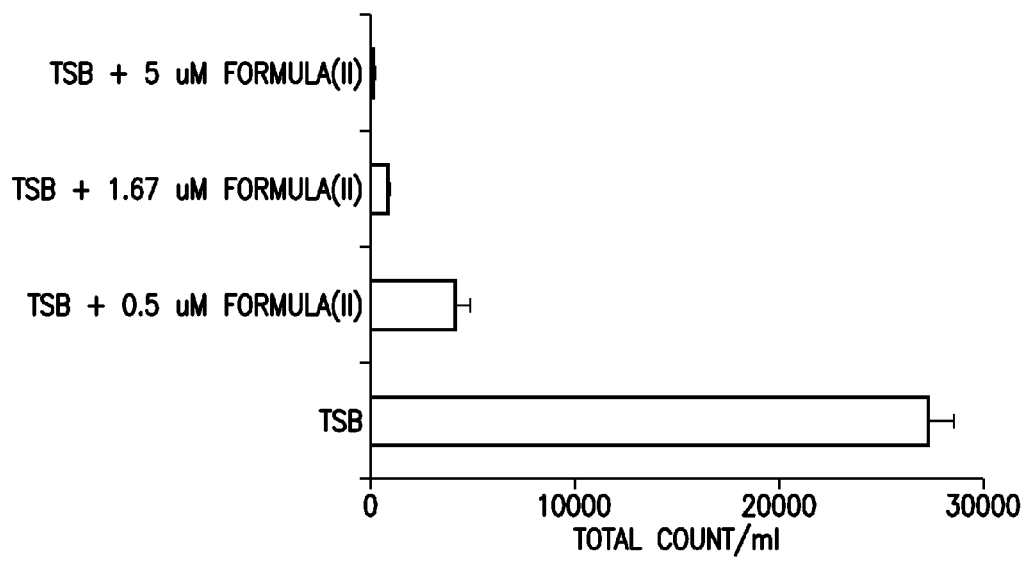
FIG. 3 reports the amount of background signal in samples treated with or without Molecule of Formula (II) at various concentrations.

Molecule of Formula (II) was added to TSB to a final concentration of either 0.5 µM, 1.67 µM, or 5 µM. The mixtures were incubated for 60 minutes prior to the addition of nucleic acid stain Syto® 62 at 0.2 µM final concentration. The mixtures were analyzed by flow cytometry. As a control, a sample containing only TSB and nucleic acid stain and not Molecule of Formula (II) was also tested. The results are summarized in FIG. 3 and demonstrate that reduction in background signal is dependent on the concentration of background signal-reducing molecule. In addition, the background signal is reduced by at least 82% with the lowest concentration of background signal-reducing molecule.

Example 4

Figure 4:
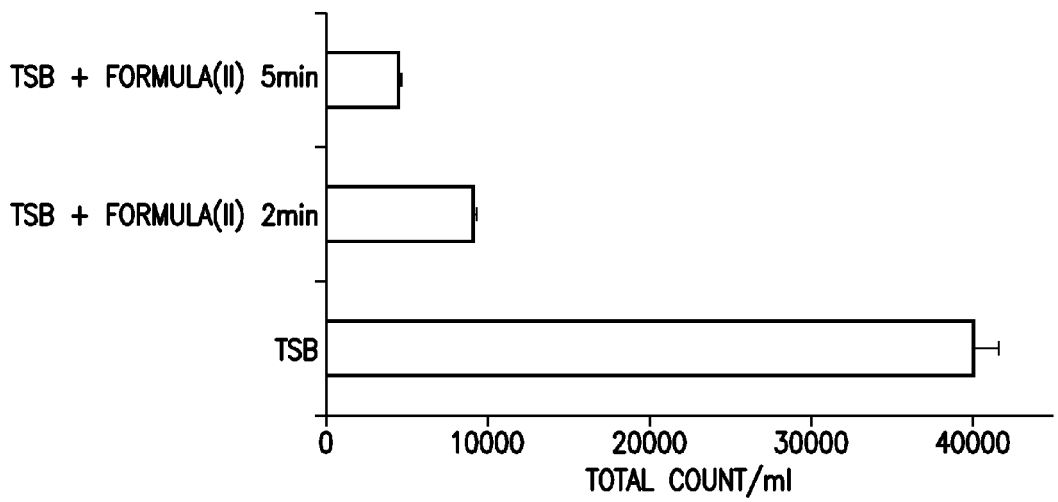
FIG. 4 reports the amount of background signal in TSB samples treated with or without Molecule of Formula (II) incubated at various time points prior to the addition of a nucleic acid stain.
Figure 5A:
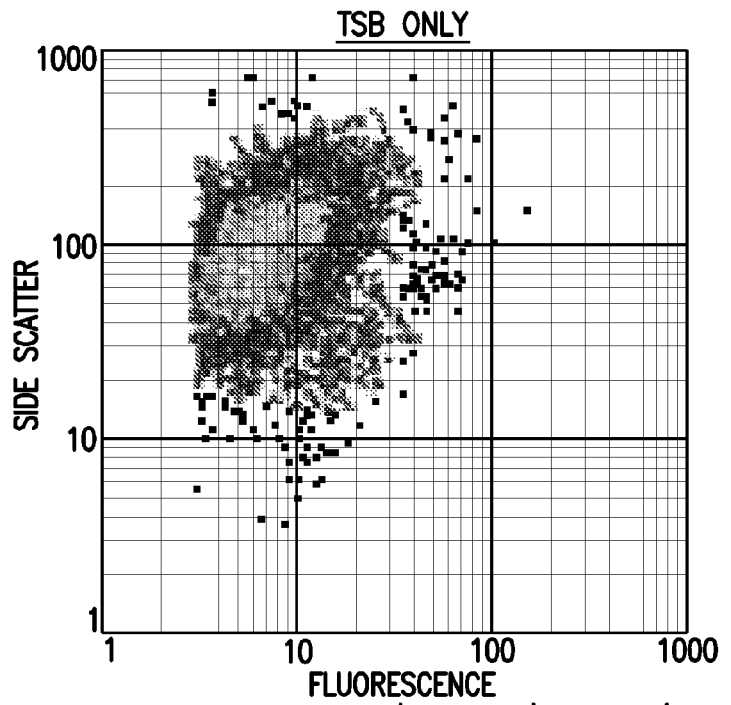
FIGS. 5A-5E report the amount of background signal in TSB samples treated with or without Molecules of Formula (I), (III), or (IV).
Figure 5B:
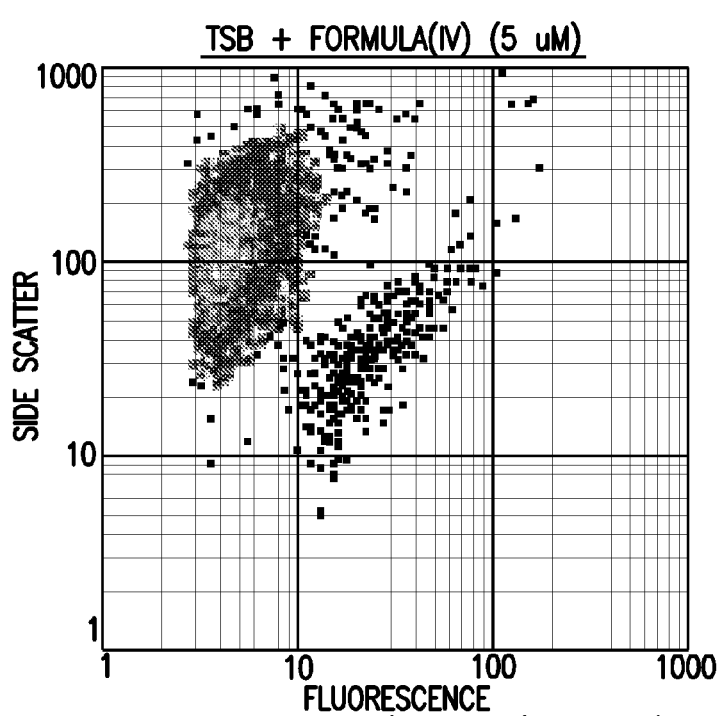
Figure 5C:
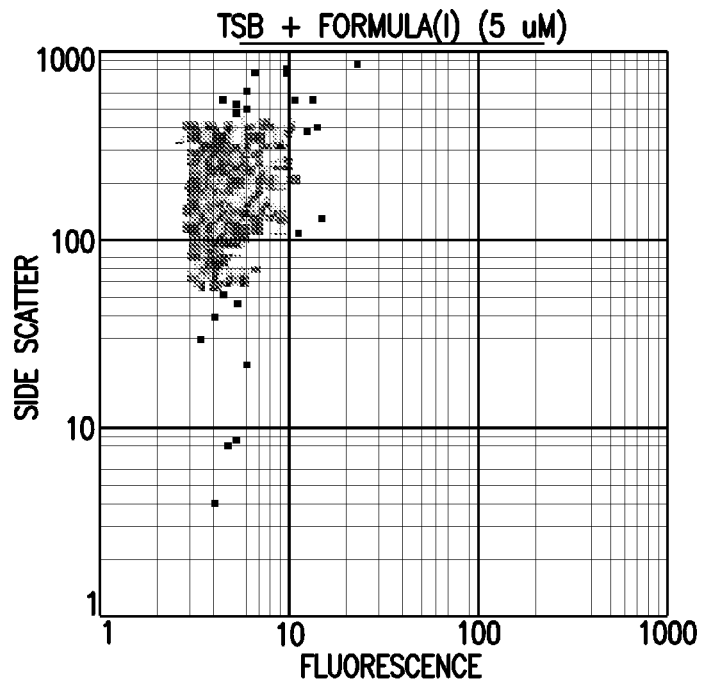
Figure 5D:
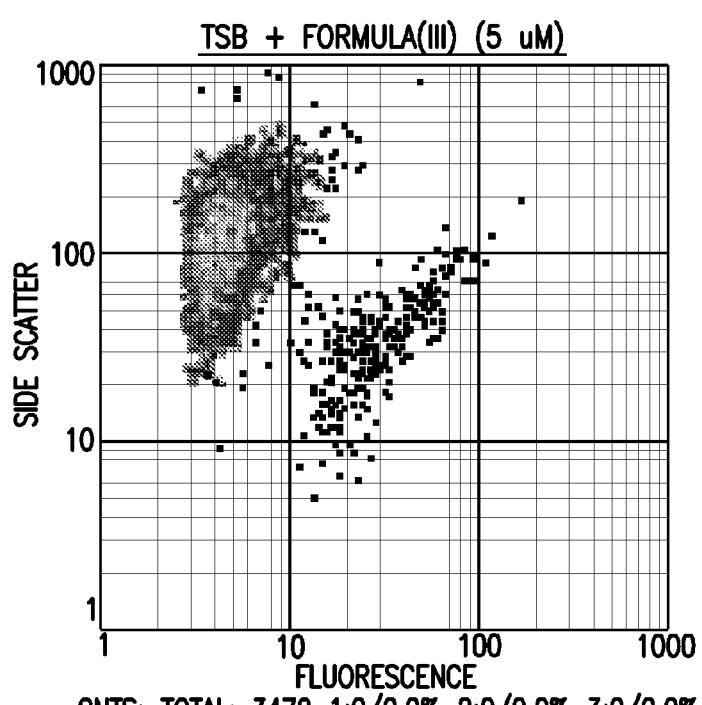
Figure 5E:
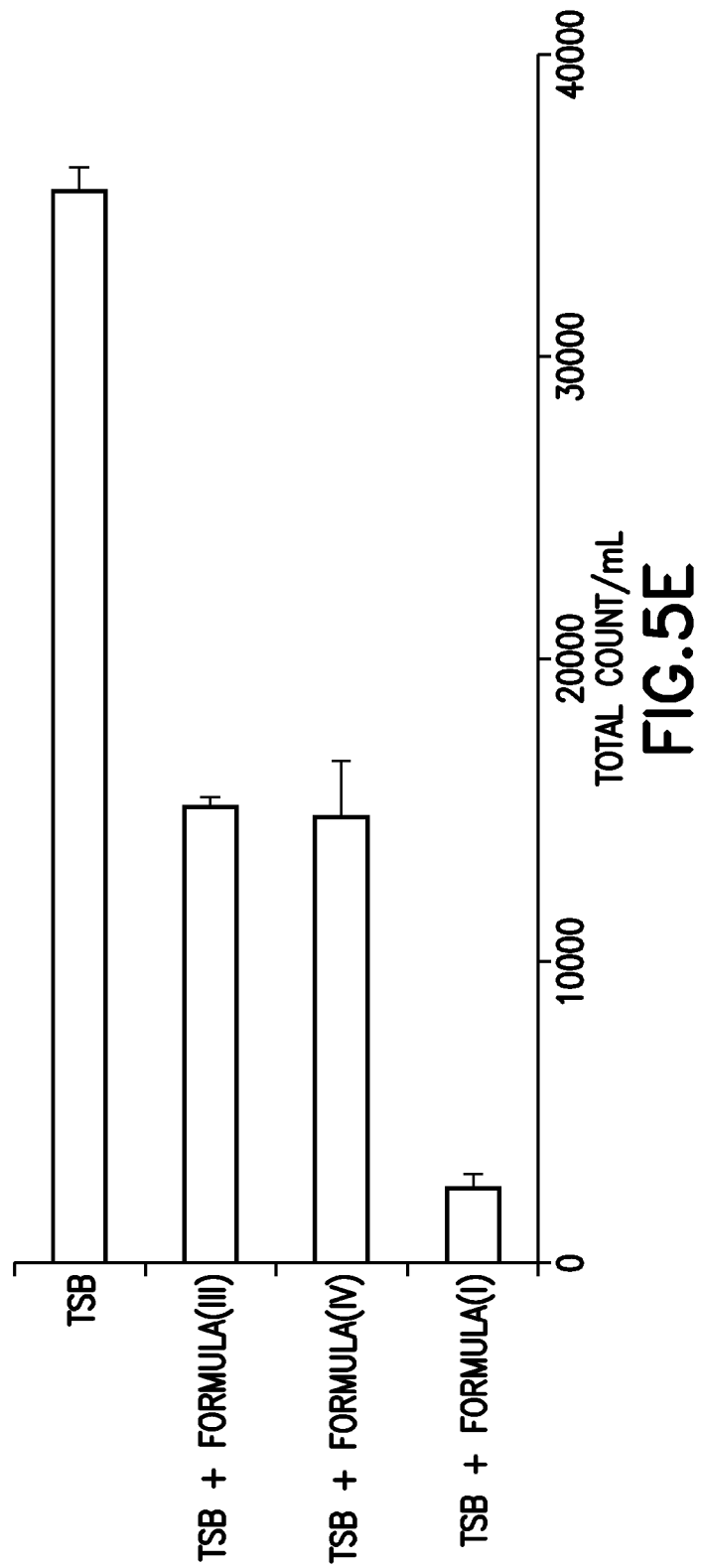
Figure 6A:
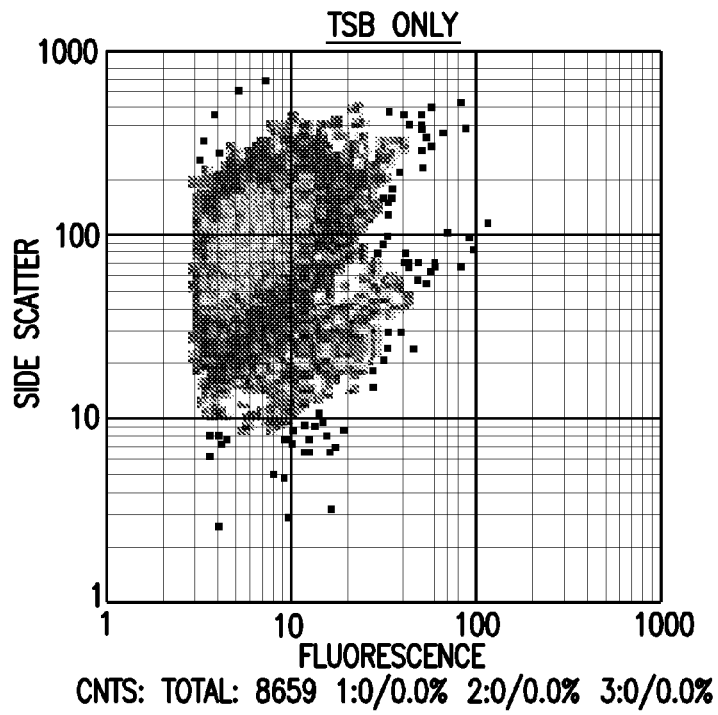
FIGS. 6A-6D report the amount of background signal in TSB samples treated with or without Molecule of Formula (I) added prior to or simultaneously with a nucleic acid stain.
Figure 6B:
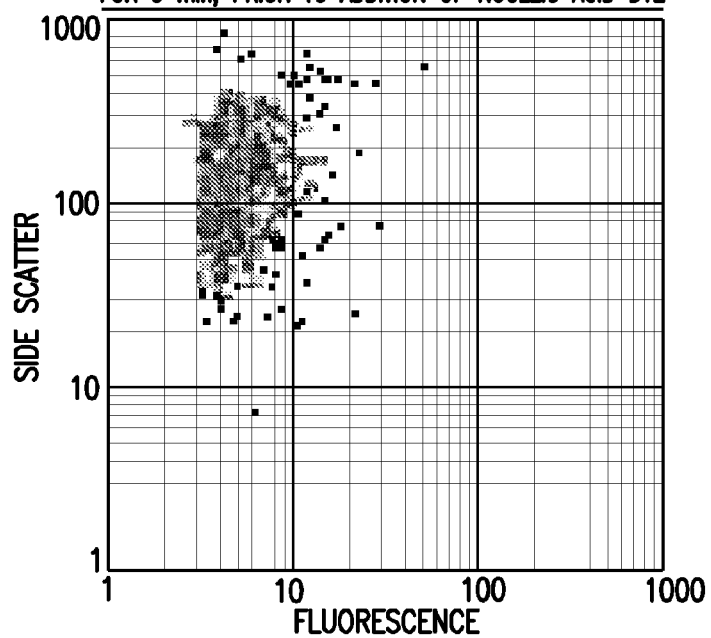
Figure 6C:
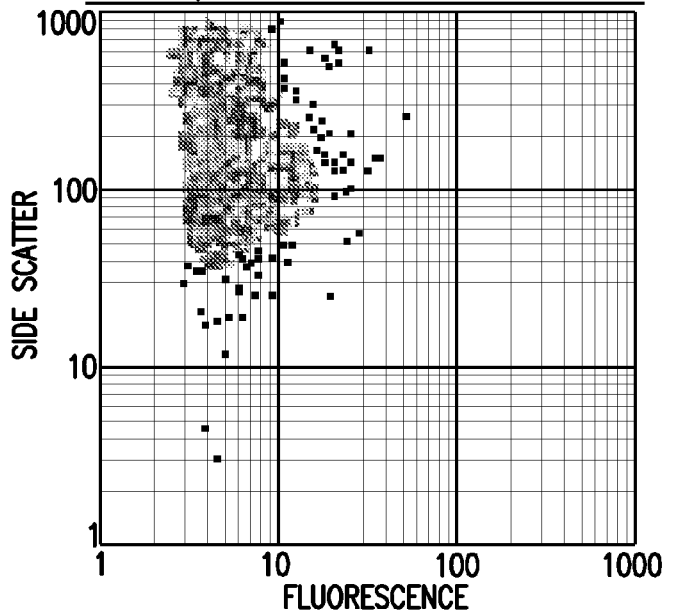
Figure 6D:
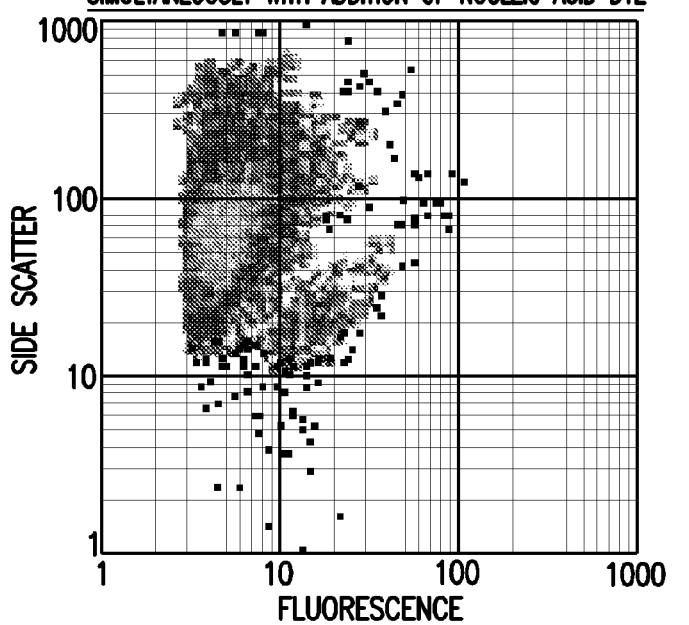
Figure 7A:
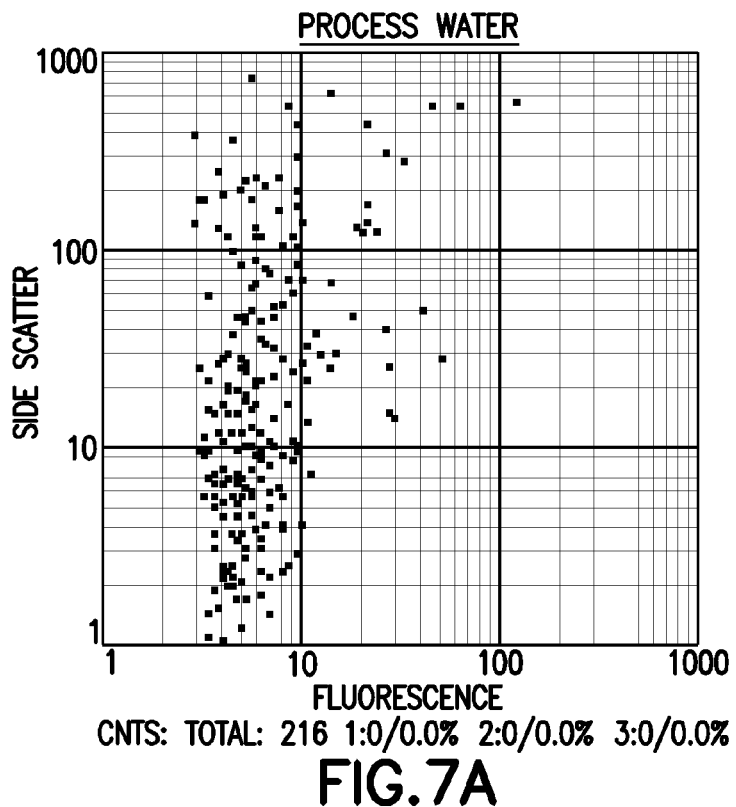
FIGS. 7A-7D report the amount of background signal in process water samples treated with or without Molecules of Formula (I) or (II).
Figure 7B:
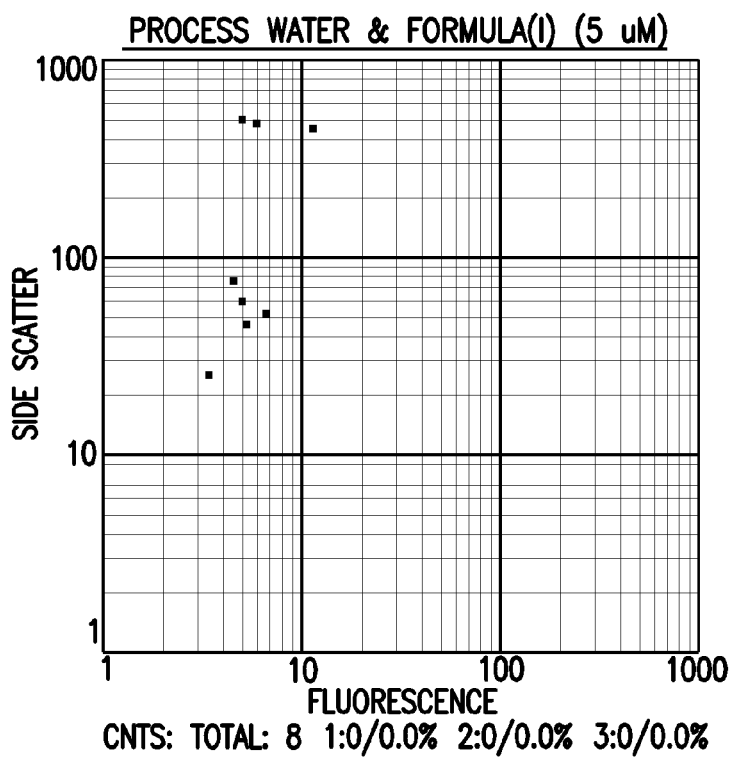
Figure 7C:
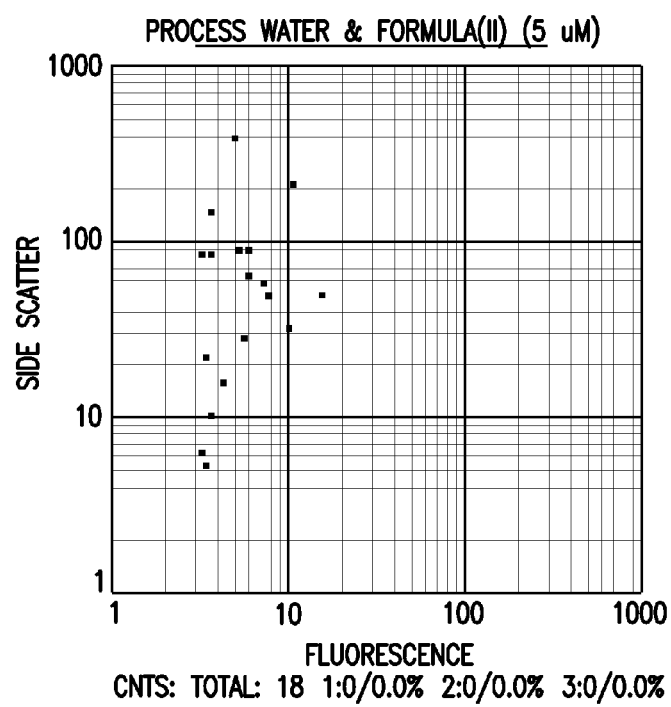
Figure 7D:
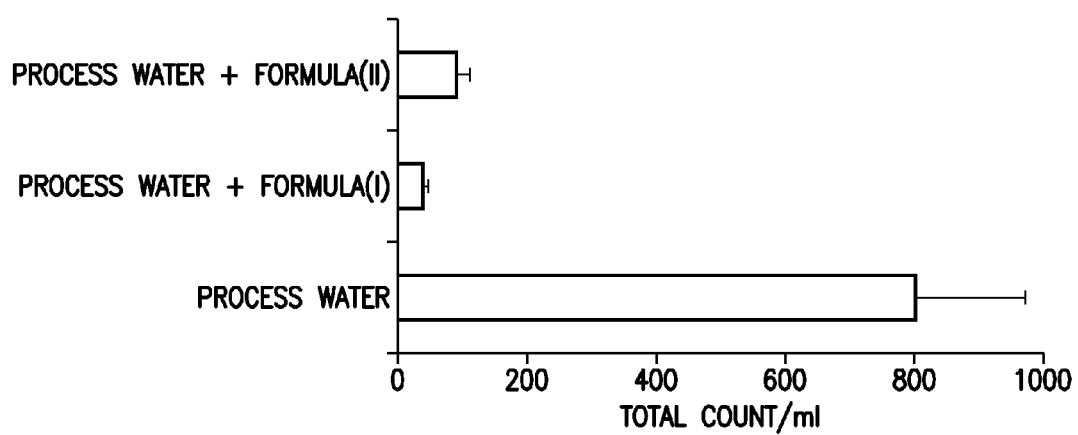
Figure 8A:
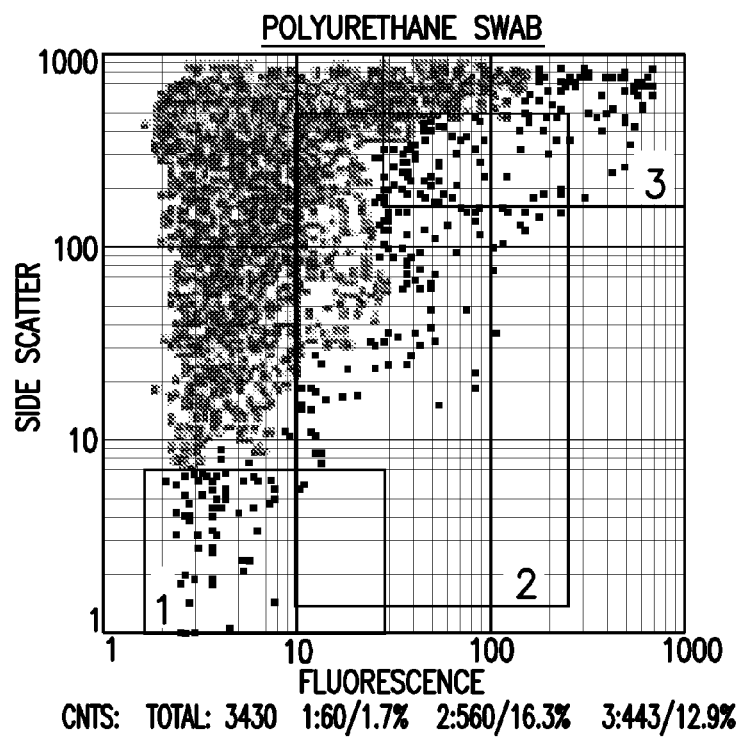
FIGS. 8A-8F report the amount of background signal in swab samples treated with or without Molecule of Formula (I).
Figure 8B:
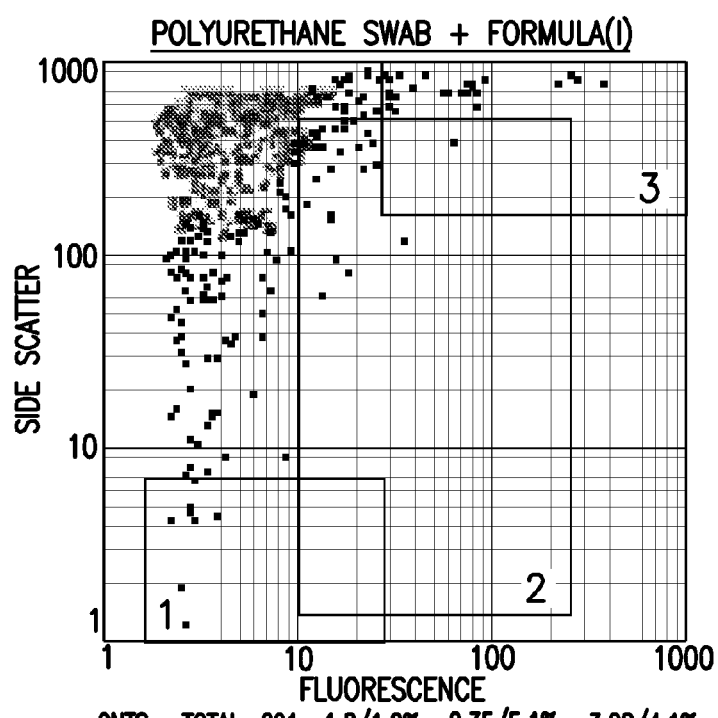
Figure 8C:
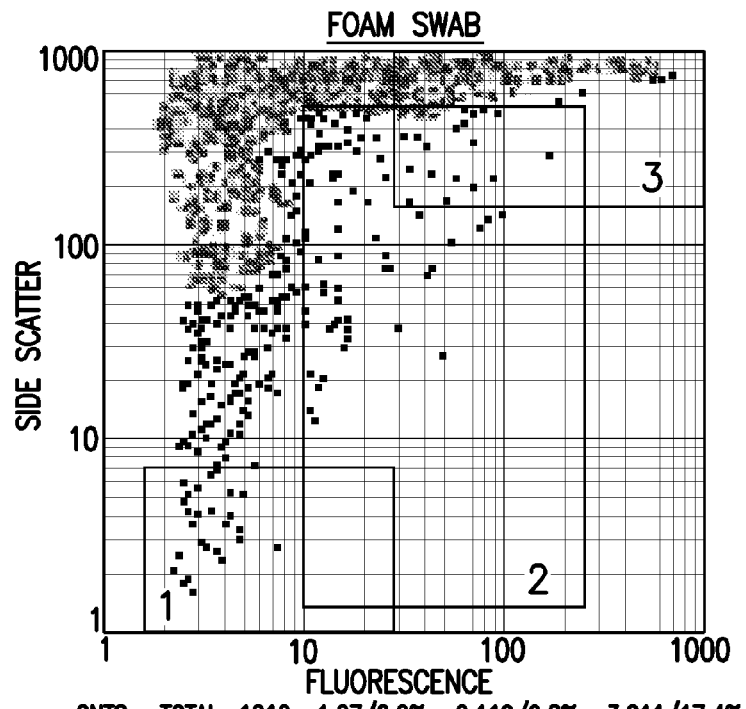
Figure 8D:
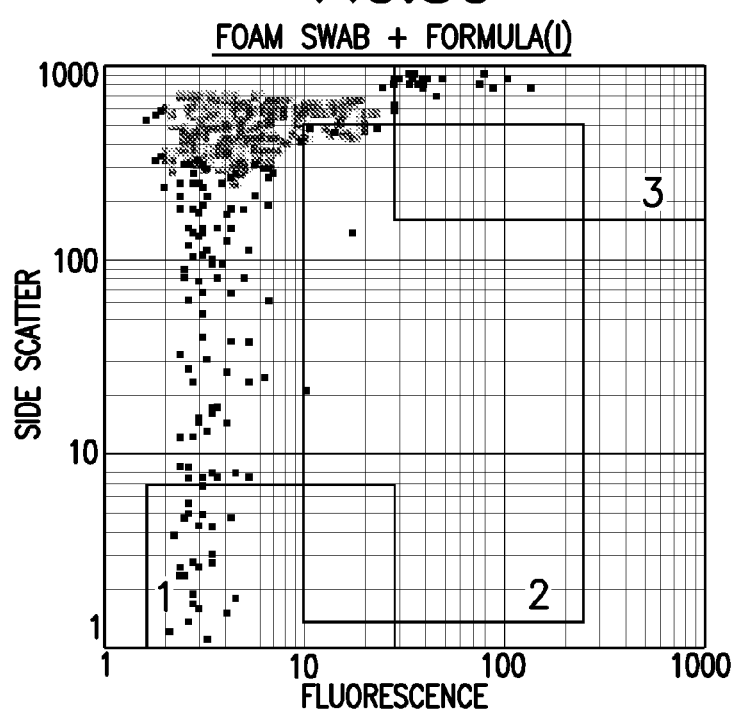
Figure 8E:
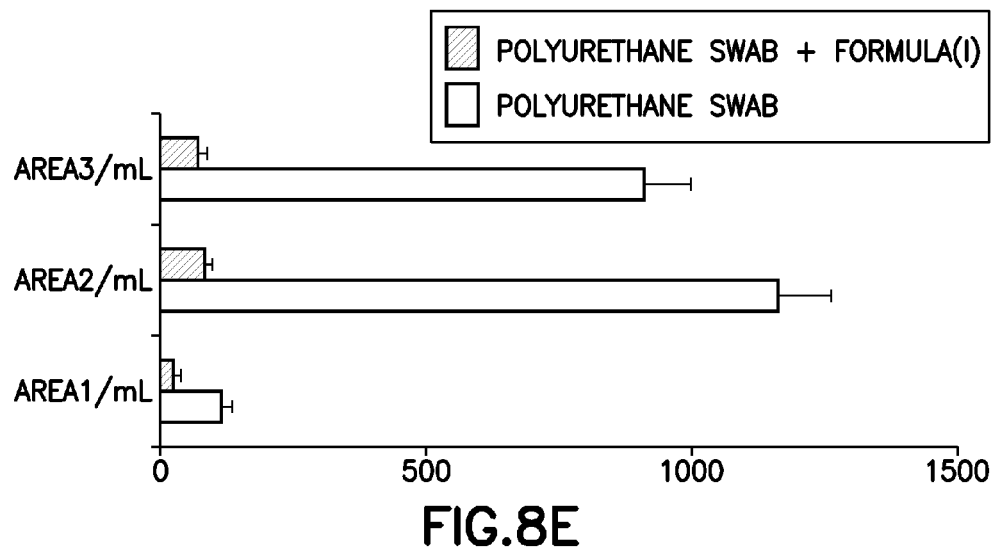
Figure 8F:
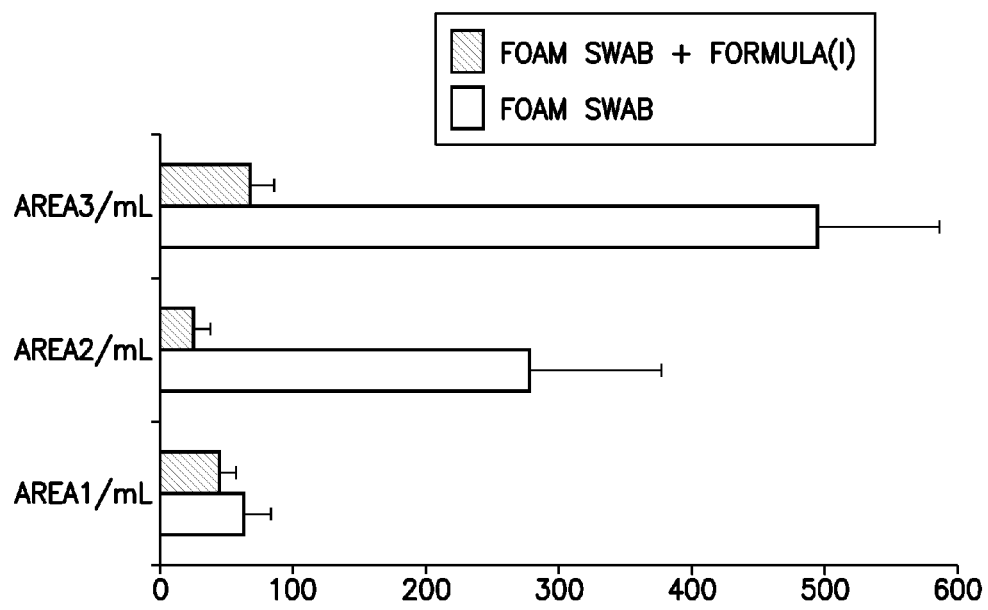

Molecule of Formula (II) was added to TSB to a final concentration of 5 µM. The mixture was incubated for either 2 minutes or 5 minutes prior to the addition of nucleic acid stain Syto® 62 at 0.2 µM final concentration. The mixtures were analyzed by flow cytometry. As a control, a sample containing only TSB and nucleic acid stain and not Molecule of Formula (II) was also tested. The results are summarized in FIG. 4 and demonstrate that reduction in background signal is dependent on the time of incubation with the background signal-reducing molecule. In addition, the background signal is reduced by at least 75% with a 2 minute incubation time.

Example 5

Molecules of Formula (I), (III), and (IV) were added to TSB to make a final concentration of molecule of 5 µM. The mixtures were incubated for 30 minutes prior to the addition of nucleic acid stain Syto® 62 at 0.2 µM final concentration. The mixture was analyzed by flow cytometry. As a control, a sample containing only TSB and nucleic acid stain and not a background signal-reducing molecule was also tested. The results are summarized in FIGS. 5A-5E. Each of the background signal-reducing molecules reduces the background signal in flow cytometry analysis by at least 55% percent and as much as up to 94%.

Example 6

Molecule of Formula (I) was added to TSB to make a final concentration of molecule of 5 µM. The mixture was either incubated for either 2 minutes or 5 minutes prior to the addition of nucleic acid stain Syto® 62 at 0.2 µM final concentration or added simultaneously with the nucleic acid stain without pre-incubation. The mixtures were analyzed by flow cytometry. As a control, a sample containing only TSB and nucleic acid stain and not Molecule of Formula (I) was also tested. The results are summarized in FIGS. 6A-6D and demonstrate that the background signal is reduced in all samples containing a background signal-reducing molecule. For the sample in which the background signal-reducing molecule is mixed simultaneously with the nucleic acid stain, the background signal was reduced by approximately 34%. The amount of reduction in background signal increased when the sample was pre-incubated with the background signal-reducing molecule prior to the addition of the nucleic acid stain. The background signal was reduced by approximately 89% and 93% for samples incubated at 5 minutes and 2 minutes respectively.

Example 7

Molecules of Formulas (I) and (II) were added to process water to make a final concentration of molecule at 5 µM. The mixtures were incubated for 30 minutes prior to the addition of nucleic acid stain Syto® 62 at 0.2 µM final concentration. The mixtures were then analyzed by flow cytometry. As a control, a sample containing only process water and nucleic acid stain, and not Molecules of Formula (I) and (II) was also tested. The results are summarized in FIGS. 7A-7D and demonstrate that the background signal is reduced to close to zero when a sample comprising process water is incubated with the background signal-reducing molecules described herein prior to flow cytometric analysis.

Example 8

The background signal-reducing molecules described herein were used to reduce the background signal from various swab samples. Swabs made of either polyurethane or foam were incubated in a solution of Molecule of Formula (I) at a final concentration of 5 µM for 30 minutes. Nucleic acid stain Syto® 62 at 0.2 µM final concentration was then added to the mixture. The mixtures were analyzed by flow cytometry. As a control, a sample containing only swab and nucleic acid stain and not Molecule of Formula (I) was also tested. Three areas were analyzed, area 1, area 2, and area 3 which represent the areas typically populated by mold, bacteria, and yeast, respectively. The results are summarized in FIGS. 8A-8F and demonstrate that the background signal is significantly reduced in each area for both types of swabs.

Example 9

Figure 9A:
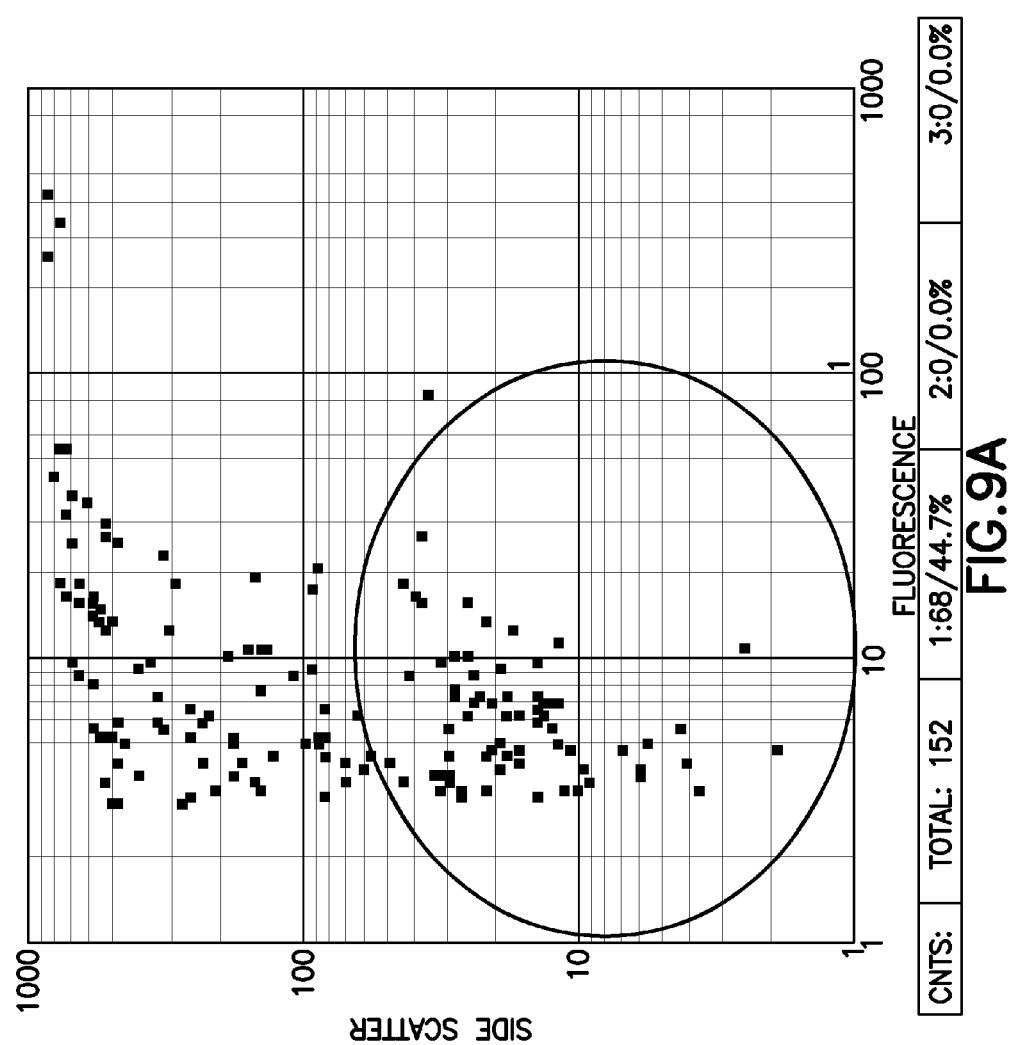
FIGS. 9A and 9B show an intensity plot for a flow cytometry analysis reporting the concentration of viable organisms using a standard water testing method on a BD FACSMicroCount with or without 5 μM Propidium Iodide.

Purified water sample with no viable organisms was used on the BD FACSMicroCount for flow cytometry analysis. Standard BD MicroCount TVO reagents (Buffer Reagent, Biomass Stain which is a cell permeable nucleic acid intercalating fluorescent dye, BRAG3) were added to the samples and subsequently analyzed by the instrument. As illustrated in FIG. 9A, the events in the circled gate area in the intensity plot are calculated to report the concentration of viable organisms (counts/ml).

Using the standard water testing method on the instrument, 290 counts/ml in the gate were reported as the total viable organism concentration in this water sample, as seen in FIG. 9A. However, no bacterial colonies could be found on R2A agar plate after the water sample was plated and incubated in an incubator for 10 days. The particles in the gate represent background particles that bind to the Biomass Stain non-specifically and fluoresce.

Figure 9B:
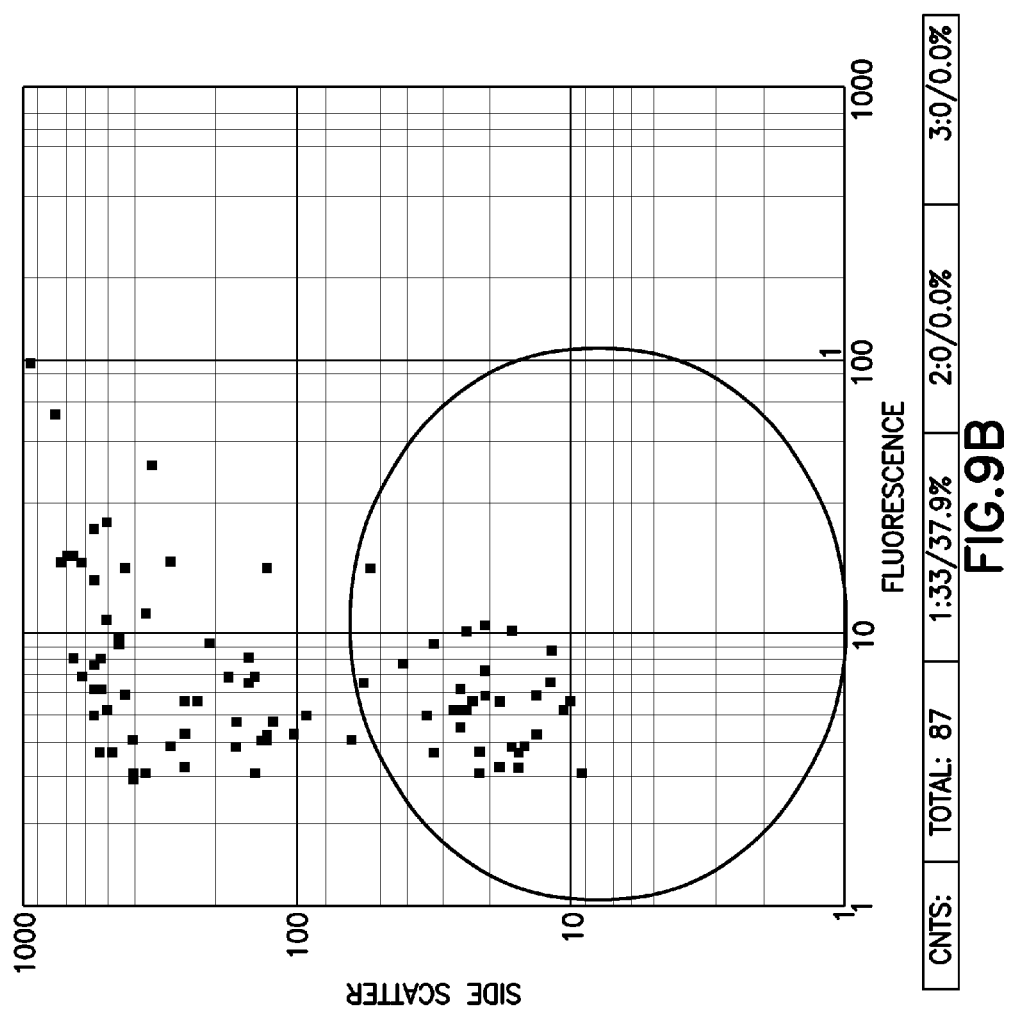

5 µM of Propidium Iodide (PI) was added to the same lot of the water sample prior to the addition of the MicroCount Biomass Stain. The same setting of the instrument was used to analyze the water sample. 152 total counts in the gate, as seen in FIG. 9B, was reported as the total viable organism concentration in the sample. In this case, since PI is also a nucleic acid intercalating molecule, excess amounts of PI can block the binding of the Biomass Stain and reduce the background counts. Although PI is a fluorescent dye, the fluorescence feature of the molecule is not needed for this study. As PI cannot be excited by the red laser in the FACSMicroCount system, the fluorescence feature of PI also does not interfere with the MicroCount Biomass Stain.

Example 10

Figure 10B:
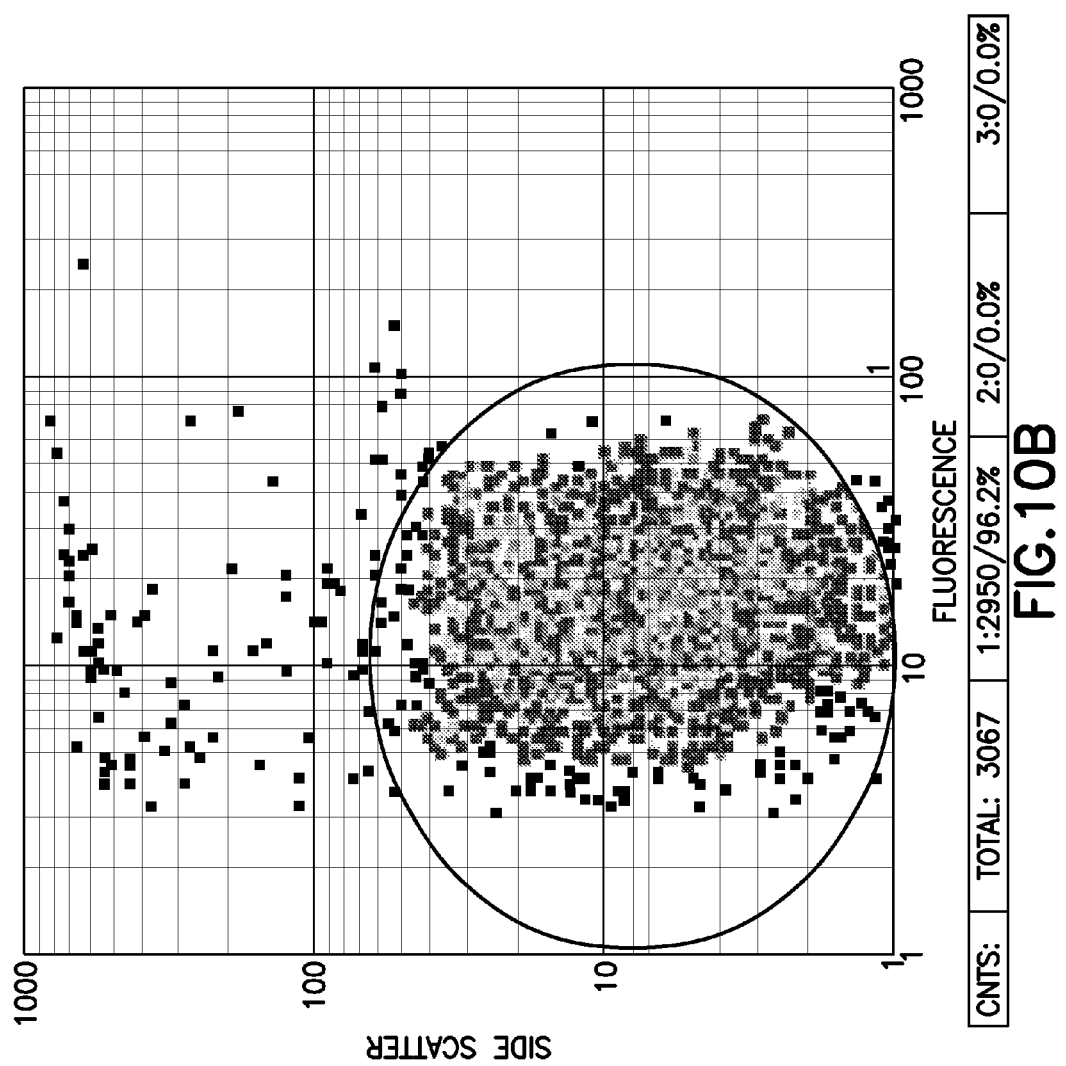

Approximately 15,000 cfu/ml of *Escherichia coli* (*E. coli*) was spiked in the water sample, and the spiked sample was analyzed by the FACMicroCount using the standard water testing method. 3283 total counts in the gate was reported as the total viable organism concentration. The results are shown in FIG. 10A.

Approximately 15,000 cfu/ml of *E. coli* was spiked in the water sample, and 5 µM PI was added to the sample prior to the addition of the Biomass Stain. 3067 total counts in the gate was reported as the total viable organism concentration, and the result was comparable to the result from sample without the addition of PI. The results are shown in FIG. 10A. Since PI is not permeable to live *E. coli* cells while the Biomass Stain is a cell permeable dye, the addition of PI does not interfere with the staining of the viable bacteria cells by the Biomass Stain.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of analyzing a sample for the total amount of viable microorganisms, comprising:
   obtaining a sample to be tested for the total viable amount of an at least one target microorganism;
   preparing the sample by:
   i) adding an excess amount of background signal-reducing molecules wherein the background signal-reducing molecule is selected from the group consisting of a molecule with the structure Y—(CH═CH)$_n$—CH═Z or salts thereof, wherein,
   Y is:

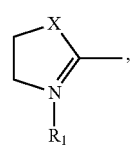

and is either substituted or unsubstituted;

n is 0 or an integer up to about 5;

X is either carbon or sulfur;

$R_1$ is optionally hydrogen, an alkyl group having from 1-6 carbon atoms, a sulfite moiety or an alkyl amide, and may be selected in order to decrease cell permeability of the background-signal reducing molecule into the viable target microorganism; and, Z is either the same or different from Y; and ii) adding a nucleic acid stain that permeates and labels target viable cells of the microorganism;

and analyzing the prepared sample for total viable amount of the at least one microorganism using flow cytometry.

2. The method of claim 1, wherein the sample is selected from the group consisting of a food sample, an environmental sample, a cosmetic sample, and a biological sample.

3. The method of claim 1, wherein the concentration of the background signal-reducing molecules is about 0.1 µM to about 50 µM when combined with the sample.

4. The method of claim 1, wherein the background signal-reducing molecules are incubated with the sample for about 2 minutes to about 1 hour prior to the addition of the nucleic acid stain.

5. The method of claim 1, wherein a quencher is attached to the background signal-reducing molecule.

6. The method of claim 1, wherein the background signal-reducing molecule is a hemicyanine or closed chain cyanine.

7. The method of claim 1, wherein n is 0 or an integer up to about 3.

8. The method of claim 1, wherein Y is selected from the group consisting of a benzene moiety fused thereto; a benzene moiety derivative fused thereto; and a quinolone substituent, wherein the benzene moiety, benzene moiety derivative, and quinolone can be substituted or unsubstituted.

9. The method of claim 8, wherein n is 0 or an integer up to about 3; X is sulfur, $R_1$ is an alkyl amide; and Y has a benzene or benzene derivative fused thereto.

10. The method of claim 1, wherein the background signal-reducing molecule is selected from the group consisting of

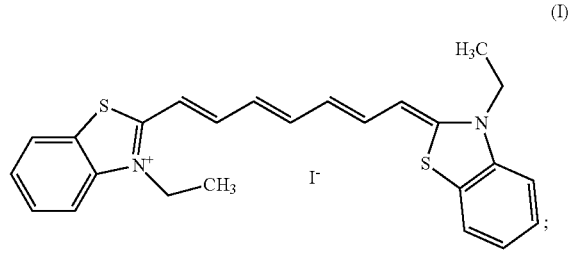

(I)

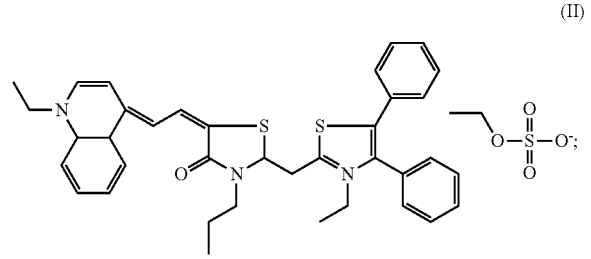

(II)

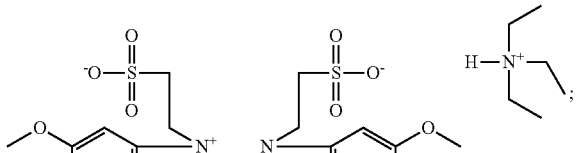

(III)

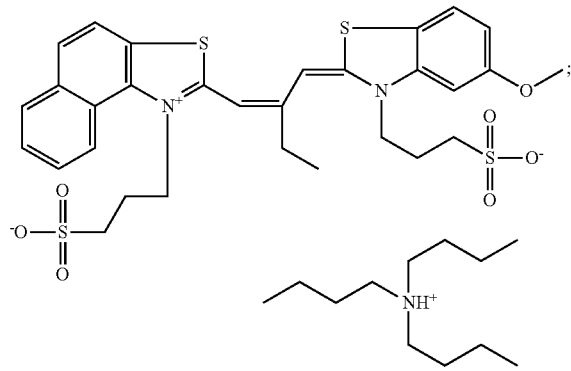

(IV)

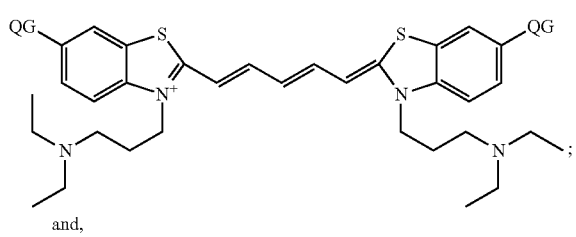

(V)

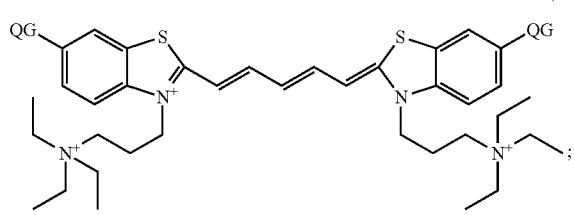

(VI)

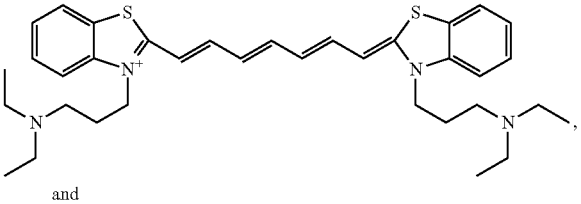

(VII)

and

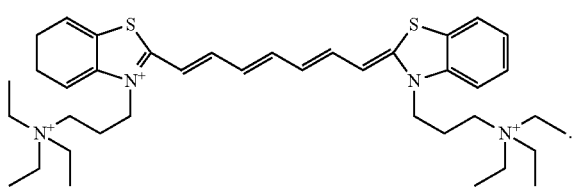

(VIII)

11. The method of claim 1, wherein the prepared sample is analyzed by flow cytometry.

12. The method of claim 11, wherein the background signal intensity is reduced by at least 50% to at least 90%.

13. The method of claim 1, wherein the sample is prepared by adding resin to the sample and removing the resin from the sample thereby removing at least a portion of particulate matter in the sample.

\* \* \* \* \*